United States Patent [19]

Farge et al.

[11] 4,385,181

[45] May 24, 1983

[54] THIOLOESTERS

[75] Inventors: Daniel Farge; Pierre L. Roy, both of Thiais; Claude Moutonnier, Le Plessis Robinson; Jean-Francois Peyronel, Palaiseau, all of France

[73] Assignee: Rhone Poulenc Industries, France

[21] Appl. No.: 233,109

[22] Filed: Feb. 10, 1981

[30] Foreign Application Priority Data

Feb. 12, 1980 [FR] France .................................. 80 03057
May 13, 1980 [FR] France .................................. 80 10706

[51] Int. Cl.³ .................. C07D 277/46; C07D 417/12; C07D 487/04; C07D 277/38
[52] U.S. Cl. .................................. 544/182; 544/316; 544/239; 544/235; 548/194; 548/136; 548/129; 548/144; 546/280
[58] Field of Search ............... 544/182, 316, 239, 235; 548/194, 136, 129, 144; 546/280

[56] References Cited

FOREIGN PATENT DOCUMENTS 862300  6/1978  Belgium .
  4570 10/1979  European Pat. Off. .
2804040  8/1979  Fed. Rep. of Germany .
2346014 10/1977  France .

*Primary Examiner*—John M. Ford
*Attorney, Agent, or Firm*—Stevens, Davis, Miller & Mosher

[57] ABSTRACT

New thioloesters of the formula:

$$\begin{array}{c} R'NH \\ \phantom{xxx} \diagdown \\ \phantom{xx} N \underline{\phantom{xxx}} \end{array} \begin{array}{c} S \\ \diagdown \\ C-CO-S-R \\ \| \\ N \\ \diagdown OR° \end{array}$$

wherein R° represents hydrogen, alkyl, vinyl, cyanomethyl or a protecting radical, R' represents hydrogen or a protecting radical, R represents alkyl, L-2-amino-2-carboxyethyl, phenyl or various heterocyclic radicals, and their syn and anti isomers and mixtures thereof, and metal salts thereof and addition salts thereof with tertiary nitrogen-containing bases, are intermediates useful in the preparation of cephalosporins having anti-bacterial properties.

10 Claims, No Drawings

THIOLOESTERS

DESCRIPTION

This invention relates to new thioloesters, useful as intermediates in the preparation of antibacterial cephalosporins, and to processes for their preparation.

European Patent Application No. 4,570 describes compounds of the general formula

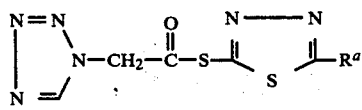

wherein $R^a$ represents hydrogen or methyl, which compounds are, in particular, useful as intermediates for the preparation of cephalosporins.

Belgian Pat. No. 862,300 describes acids of the general formula

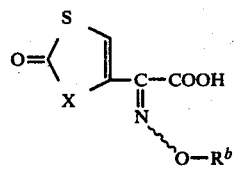

wherein X represents, inter alia, imino, and $R^b$ represents hydrogen or a saturated or unsaturated aliphatic hydrocarbon radical and their reactive derivatives, in particular the thioesters, such as the phenyl, p-nitrophenyl, p-cresyl and carboxymethyl thioesters, which are used for the preparation of cephalosporins.

The present invention provides thioloesters of the general formula:

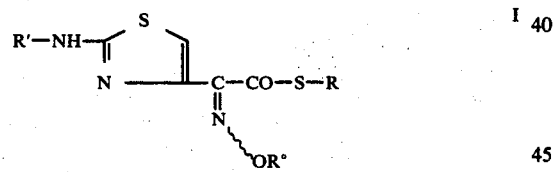

wherein R represents (1) alkyl, L-2-amino-2-carboxyethyl or phenyl;

(2) pyrid-2-yl, pyrid-3-yl or pyrid-4-yl or their N-oxides;

(3) pyrimidin-2-yl, pyridazin-3-yl substituted in the 6-position by an alkyl, methoxy, amino or acylamino radical and optionally N-oxidised, or tetrazolo[4,5-b]pyridazin-6-yl;

(4) 5,6-dioxo-1,4,5,6-tetrahydro-1,2,4-triazin-3-yl substituted in the 4-position, or 1,3,4-triazol-5-yl or 2-alkoxycarbonyl-1,3,4-triazol-5-yl substituted in the 1-position, (a) by an alkyl radical which is unsubstituted or substituted by an alkoxy, alkylthio, phenyl, carbamoyl, alkylcarbamoyl, dialkylcarbamoyl, acyl, alkoxycarbonyl or thiazolidin-2-yl radical, (b) by an allyl, 2,3-dihydroxypropyl, 1,3-dihydroxyprop-2-yl, 3-formyloxy-2-hydroxypropyl, 2,3-bis-formyloxypropyl or 1,3-bis-formyloxyprop-2-yl radical, (c) by an alkyl radical containing 2 to 4 carbon atoms and substituted by a hydroxy or carbamoyloxy radical, an acyloxy radical (in which the acyl moiety can be substituted by an amino, alkylamino or dialkylamino radical), an alkylsulphinyl, alkylsulphonyl, amino, alkylamino, dialkylamino, sulphoamino, alkylsulphonylamino or sulphamoylamino radical, an acylamino radical (in which the acyl moiety is optionally substituted by hydroxy, amino, alkylamino or dialkylamino) or an alkoxycarbonylamino, ureido, alkylureido or dialkylureido radical, (d) by a radical of the general formula:

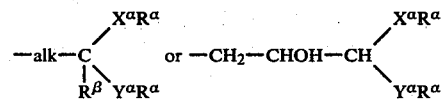

wherein alk represents an alkylene radical containing 1 to 4 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or an alkyl radical containing 1 to 3 carbon atoms, or (e) by an alkyl radical containing 2 to 5 carbon atoms and substituted by an alkoxyimino or hydroxyimino radical;

(5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl;

(6) 1,3,4-triazol-5-yl, 1,2,3-triazol-5-yl or 1-alkyl-1,2,4-triazol-5-yl which is unsubstituted or substituted in the 3-position by alkoxycarbonyl;

(7)(a) 1,3,4-thiadiazol-5-yl which is unsubstituted or substituted by an alkyl, trifluoromethyl, alkoxy or alkylthio radical, a hydroxyalkylthio radical in which the alkyl moiety contains 2 to 4 carbon atoms, or an alkylsulphonyl, hydroxy, hydroxyalkyl, carboxy, carboxyalkyl, amino, alkylamino, dialkylamino, aminoalkyl, alkylaminoalkyl, dialkylaminoalkyl, acylamino or acylaminoalkyl radical, or (b) 1,2,4-thiadiazol-5-yl substituted by an alkyl or alkoxy radical;

(8)(a) 1,3,4-oxadiazol-5-yl which is unsubstituted or substituted by an alkyl, trifluoromethyl, phenyl, aminoalkyl, alkylaminoalkyl, dialkylaminoalkyl or acylaminoalkyl radical, or (b) oxazol-2-yl or 4-alkyloxazol-2-yl; or (9) tetrazol-5-yl which is unsubstituted or substituted in the 1-position by (a) an alkyl radical which is unsubstituted or substituted by alkoxy, sulpho, carboxy or sulphamoyl, (b) an alkyl radical containing 2 to 4 carbon atoms and substituted by hydroxy, amino, alkylamino, dialkylamino, acylamino, carboxyalkylamino, sulphamoylamino, sulphoamino, ureido, alkylureido or dialkylureido, (c) an alkyl radical containing 2 to 5 carbon atoms and substituted by hydroxyimino or alkoxyimino, (d) a phenyl, 2,3-dihydroxypropyl, 1,3-dihydroxyprop-2-yl, 3-formyloxy-2-hydroxypropyl, 2,3-bisformyloxypropyl or 1,3-bis-formyloxyprop-2-yl radical, or (e) a radical of general formula II wherein $R^\beta$ represents a hydrogen atom, or a radical of general formula III;

R° represents a hydrogen atom, an alkyl, vinyl or cyanomethyl radical or a protecting radical and R' represents a hydrogen atom or a protecting radical preferably selected from t-butoxycarbonyl, 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, trifluoroacetyl and formyl; and, when R contains a carboxy or sulpho radical, metal salts thereof and addition salts thereof with tertiary nitrogen-containing bases.

It is understood that, in the above definitions, the amino or alkylamino groups which exist in certain radicals R are protected, and that the carboxy and hydroxy groups are optionally protected.

Protection is carried out by means of any group which is normally used for protecting amines, carboxylic acids or alcohols, and the use of which does not adversely affect the rest of the molecule.

By way of examples, the amino and alkylamino groups are protected by radicals such as the protecting radicals hereinbefore specified for R';

the carboxy groups can be protected by radicals such as methoxymethyl, t-butyl, benzhydryl, p-nitrobenzyl or p-methoxybenzyl; and the hydroxy groups can be protected by radicals such as trityl, tetrahydropyranyl or 2-methoxyprop-2-yl, or alternatively in the form of a 2,2-dimethyldioxolan-4-yl-methyl or 2,2-dimethyldioxan-5-yl radical in the case of the protection of the 2,3-dihydroxypropyl or 1,3-dihydroxyprop-2-yl radicals.

It is to be understood that alkyl and acyl moieties or radicals in this specification and the accompanying claims are linear or branched and unless otherwise specified contain from 1 to 4 carbon atoms.

The group —OR° in the compounds of general formula I can be in either the syn or anti configuration and these isomers and their mixtures fall within the scope of the present invention.

The syn form can be represented by the general formula:

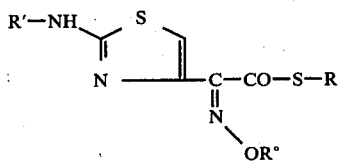
Ia

The anti form can be represented by the general formula:

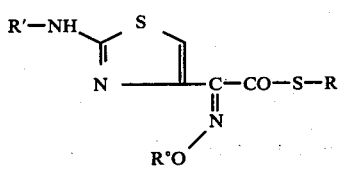
Ib

Similarly, if the radical R contains a hydroxyiminoalkyl or alkoxyiminoalkyl substituent, this substituent can exhibit syn/anti isomerism and these isomers and their mixtures also fall within the scope of the present invention.

When the radical R represents a 5,6-dioxo-1,4,5,6-tetrahydrotriazinyl radical substituted in the 1- or 4-position or a 5,6-dioxo-1,2,5,6-tetrahydrotriazinyl radical substituted in the 2-position, the tautomeric forms can be represented by formulae IVa and formulae IVb and IVc, respectively:

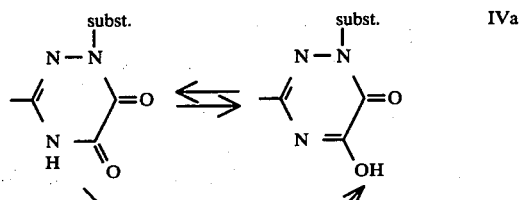
IVa

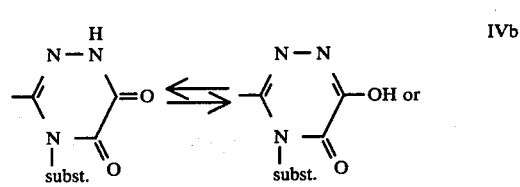
IVb

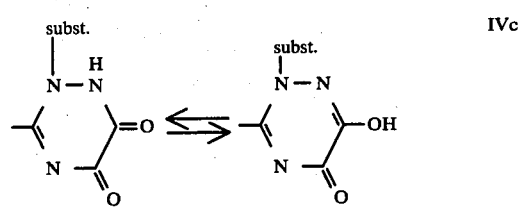
IVc wherein subst. represents the substituent.

Amongst the above meanings of the radical R, the following may be mentioned in particular: methyl, ethyl, propyl, isopropyl, butyl, isobutyl, sec.-butyl, t-butyl, pyrid-2-yl, pyrid-3-yl, pyrid-4-yl, pyrid-2-yl-1-oxide, pyrimidin-2-yl, 6-methylpyridazin-3-yl-1-oxide, 6-methylpyridazin-3-yl, 6-ethylpyridazin-3-yl, 6-ethylpyridazin-3-yl-1-oxide, 6-methoxypyridazin-3-yl, 6-t-butoxycarbonylaminopyridazin-3-yl, 6-acetamidopyridazin-3-yl, tetrazolo[4,5-b]pyridazin-6-yl, 5,6-dioxo-4-methyl-1,4,5,6-tetrahydro-1,2,4-triazin-3-yl, 5,6-dioxo-4-ethyl-1,4,5,6-tetrahydro-1,2,4-triazin-3-yl, 5,6-dioxo-4-propyl-1,4,5,6-tetrahydro-1,2,4-triazin-3-yl, 5,6-dioxo-4-isopropyl-1,4,5,6-tetrahydro-1,2,4-triazin-3-yl, 4-allyl-5,6-dioxo-1,4,5,6-tetrahydro-1,2,4-triazin-3-yl, 5,6-dioxo-4-(2-hydroxyethyl)-1,4,5,6-tetrahydro-1,2,4-triazin-3-yl, 5,6-dioxo-4-methoxymethyl-1,4,5,6-tetrahydro-1,2,4-triazin-3-yl, 5,6-dioxo-4-(2-methoxyethyl)-1,4,5,6-tetrahydro-1,2,4-triazin-3-yl, 5,6-dioxo-4-ethoxymethyl-1,4,5,6-tetrahydro-1,2,4-triazin-3-yl, 5,6-dioxo-4-(2-ethoxyethyl)-1,4,5,6-tetrahydro-1,2,4-triazin-3-yl, 4-(2-acetamidoethyl)-5,6-dioxo-1,4,5,6-tetrahydro-1,2,4-triazin-3-yl, 4-benzyl-5,6-dioxo-1,4,5,6-tetrahydro-1,2,4-triazin-3-yl, 5,6-dioxo-4-phenethyl-1,4,5,6-tetrahydro-1,2,4-triazin-3-yl, 5,6-dioxo-4-methylthiomethyl-1,4,5,6-tetrahydro-1,2,4-triazin-3-yl, 5,6-dioxo-4-methylthioethyl-1,4,5,6-tetrahydro-1,2,4- triazin-3-yl, 4-carbamoylmethyl-5,6-dioxo-1,4,5,6-tetrahydro-1,2,4-triazin-3-yl, 4-(2-carbamoylethyl)-5,6-dioxo-1,4,5,6-tetrahydro-1,2,4-triazin-3-yl, 4-(3-carbamoylpropyl)-5,6-dioxo-1,4,5,6-tetrahydro-1,2,4-triazin-3-yl, 4-(2-carbamoyloxyethyl)-5,6-dioxo-1,4,5,6-tetrahydro-1,2,4-triazin-3-yl, 4-(3-carbamoyloxypropyl)-5,6-dioxo-1,4,5,6-tetrahydro-1,2,4-triazin-3-yl, 5,6-dioxo-4-methylsulphinylethyl-1,4,5,6-tetrahydro-1,2,4-triazin-3-yl, 5,6-dioxo-4-(2-formyloxyethyl)-1,4,5,6-tetrahydro-1,2,4-triazin-3-yl, 5,6-dioxo-4-(3-formyloxypropyl)-1,4,5,6-tetrahydro-1,2,4-triazin-3-yl, 4-(2-acetoxyethyl)-5,6-dioxo-1,4,5,6-tetrahydro-1,2,4-triazin-3-yl, 4-(3-acetoxypropyl)-5,6-dioxo-1,4,5,6-tetrahydro-1,2,4-triazin-3-yl, 5,6-dioxo-4-(2-t-butoxycarbonylglycyloxyethyl)-1,4,5,6-tetrahydro-1,2,4-triazin-3-yl, 5,6-dioxo-4-(3-t-butoxycarbonylglyclyoxypropyl)-1,4,5,6-tetrahydro-1,2,4-triazin-3-yl, 5,6-dioxo-4-(2-propanoyloxyethyl)-1,4,5,6-tetrahydro-1,2,4-triazin-3-yl, 4-(2,2,-dimethoxyethyl)-5,6-dioxo-1,4,5,6-tetrahydro-1,2,4-triazin-3-yl, 4-(3,3-dimethoxypropyl)-5,6-dioxo-1,4,5,6-tetrahydro-1,2,4-triazin-3-yl, 4-(2,2-diethoxyethyl)-5,6-dioxo-1,4,5,6-tetrahydro-1,2,4-triazin-3-yl, 4-(3,3-diethoxypropyl)-5,6-dioxo-1,4,5,6-tetrahydro-1,2,4-triazin-3-yl, 4-(2,2-bis-methylthioethyl)-5,6-dioxo-1,4,5,6-tetrahydro-1,2,4-triazin-3-yl, 4-(3,3-bis-methylthiopropyl)-5,6-dioxo-1,4,5,6-tetrahydro-1,2,4-triazin-3-yl, 4-(2,2-bis-ethylthioethyl)-5,6-dioxo-1,4,5,6-tetrahydro-1,2,4-triazin-3-yl, 4-(3,3-bis-ethylthiopropyl)-5,6-dioxo-1,4,5,6-tetrahydro-1,2,4-triazin-3-yl, 5,6-dioxo-4-[(1,3-dioxolan-2-yl)-methyl]-1,4,5,6-tetrahydro-1,2,4-triazin-3-yl, 5,6-dioxo-4-[2-(1,3-dioxolan-2-yl)-ethyl]-1,4,5,6-tetrahydro-1,2,4-triazin-3-yl, 5,6-dioxo-4-[(1,3-dithiolan-2-yl)-methyl]-1,4,5,6-tetrahydro-1,2,4-triazin-3-yl, 5,6-dioxo-4-[(2-(1,3-dithiolan-2-yl)-ethyl]-1,4,5,6-tetrahydro-1,2,4-triazin-3-yl, 5,6-dioxo-4-[(1,3-oxathiolan-2-yl)-methyl]-1,4,5,6-tetrahydro-1,2,4-triazin-3-yl, 5,6-dioxo-4-[2-(1,3-oxathiolan-2-yl)-ethyl]-1,4,5,6-tetrahydro-1,2,4-triazin-3-yl, 5,6-dioxo-4-[(1,3-dioxan-2-yl)-methyl]-1,4,5,6-tetrahydro-1,2,4-triazin-3-yl, 5,6-dioxo-4-[2-(1,3-dioxan-2-yl)-ethyl]-1,4,5,6-tetrahydro-1,2,4-triazin-3-yl, 5,6-dioxo-4-[(1,3-dithian-2-yl)-methyl]-1,4,5,6-tetrahydro-1,2,4-triazin-3-yl, 5,6-dioxo-4-[2-(1,3-dithian-2-yl)-ethyl]-1,4,5,6-tetrahydro-1,2,4-triazin-3-yl, 5,6-dioxo-4-methylcarbamoylmethyl-1,4,5,6-tetrahydro-1,2,4-triazin-3-yl, 5,6-dioxo-4-(2-methylcarbamoylethyl)-1,4,5,6-tetrahydro-1,2,4-triazin-3-yl, 5,6-dioxo-4-ethylcarbamoylmethyl-1,4,5,6-tetrahydro-1,2,4-triazin-3-yl, 4-dimethylcarbamoylmethyl-5,6-dioxo-1,4,5,6-tetrahydro-1,2,4-triazin-3-yl, 4-(2-dimethylcarbamoylethyl)-5,6-dioxo-1,4,5,6-tetrahydro-1,2,4-triazin-3-yl, 4-diethylcarbamoylmethyl-5,6-dioxo-1,4,5,6-tetrahydro-1,2,4-triazin-3-yl, 5,6-dioxo-4-(methoxycarbonylmethyl)-1,4,5,6-tetrahydro-1,2,4-triazin-3-yl, 5,6-dioxo-4-(2-methoxycarbonylethyl)-1,4,5,6-tetrahydro-1,2,4-triazin-3-yl, 5,6-dioxo-4-(ethoxycarbonylmethyl)-1,4,5,6-tetrahydro-1,2,4-triazin-3-yl, 4-[(2,2-dimethyldioxolan-4-yl)-methyl]-5,6-dioxo-1,4,5,6-tetrahydro-1,2,4-triazin-3-yl, 4-(2,2-dimethyldioxan-5-yl)-5,6-dioxo-1,4,5,6-tetrahydro-1,2,4-triazin-3-yl, 4-(2-t-butoxycarbonylaminoethyl)-5,6-dioxo-1,4,5,6-tetrahydro-1,2,4-triazin-3-yl, 4-(3-t-butoxycarbonylaminopropyl)-5,6-dioxo-1,4,5,6-tetrahydro-1,2,4-triazin-3-yl, 5,6-dioxo-4-[2-(N-methyl-N-t-butoxycarbonylamino)-ethyl]-1,4,5,6-tetrahydro-1,2,4-triazin-3-yl, 5,6-dioxo-4-[3-(N-methyl-N-t-butoxycarbonylamino)propyl]-1,4,5,6-tetrahydro-1,2,4-triazin-3-yl, 4-[2-(N-t-butoxycarbonyl-N-ethylamino)-ethyl]-5,6-dioxo-1,4,5,6-tetrahydro-1,2,4-triazin-3-yl, 4-[3-(N-t-butoxycarbonyl-N-ethylamino)-propyl]-5,6-dioxo-1,4,5,6-tetrahydro-1,2,4-triazin-3-yl, 4-(2-dimethylaminoethyl)-5,6-dioxo-1,4,5,6-tetrahydro-1,2,4-triazin-3-yl, 4-(3-dimethylaminopropyl)-5,6-dioxo-1,4,5,6-tetrahydro-1,2,4-triazin-3-yl, 4-(2-diethylaminoethyl)-5,6-dioxo-1,4,5,6-tetrahydro-1,2,4-triazin-3-yl, 4-(3-diethylaminopropyl)-5,6-dioxo-1,4,5,6-tetrahydro-1,2,4-triazin-3-yl, 5,6-dioxo-4-(2-sulphoaminoethyl)-1,4,5,6-tetrahydro-1,2,4-triazin-3-yl, 5,6-dioxo-4-(2-methylsulphonylaminoethyl)-1,4,5,6-tetrahydro-1,2,4-triazin-3-yl, 5,6-dioxo-4-(3-methylsulphonylaminopropyl)-1,4,5,6-tetrahydro-1,2,4-triazin-3-yl, 5,6-dioxo-4-(2-sulphamoylaminoethyl)-1,4,5,6-tetrahydro-1,2,4-triazin-3-yl, 5,6-dioxo-4-(3-sulphamoylaminopropyl)-1,4,5,6-tetrahydro-1,2,4-triazin-3-yl, 5,6-dioxo-4-(2-glycoloylaminoethyl)-1,4,5,6-tetrahydro-1,2,4-triazin-3-yl, 5,6-dioxo-4-[2-(2-hydroxypropionamido)-ethyl]-1,4,5,6-tetrahydro-1,2,4-triazin-3-yl, 5,6-dioxo-4-[2-(N-t-butoxycarbonylglycyl)-aminoethyl]-1,4,5,6-tetrahydro-1,2,4-triazin-3-yl, 4-[(L)-2-(N-t-butoxycarbonylalanyl)-aminoethyl]-5,6-dioxo-1,4,5,6-tetrahydro-1,2,4-triazin-3-yl, 4-[3-(N-t-butoxycarbonylglycyl)-aminopropyl]-5,6-dioxo-1,4,5,6-tetrahydro-1,2,4-triazin-3-yl, 4-[2-(N-t-butoxycarbonyl-N-methylamino)acetamidoethyl]-5,6-dioxo-1,4,5,6-tetrahydro-1,2,4-triazin-3-yl, 4-(2-dimethylaminoacetamidoethyl)-5,6-dioxo-1,4,5,6-tetrahydro-1,2,4-triazin-3-yl, 4-(2-diethylaminoacetamidoethyl)-5,6-dioxo-1,4,5,6-tetrahydro-1,2,4-triazin-3-yl, 5,6-dioxo-4-(2-methoxycarbonylaminoethyl)-1,4,5,6-tetrahydro-1,2,4-triazin-3-yl, 5,6-dioxo-4-(2-ethoxycarbonylaminoethyl)-1,4,5,6-tetrahydro-1,2,4-triazin-3-yl, 5,6-dioxo-1,4,5,6-tetrahydro-4-(2-ureidoethyl)-1,2,4-triazin-3-yl, 5,6-dioxo-1,4,5,6-tetrahydro-4-(3-ureidopropyl)-1,2,4-triazin-3-yl, 5,6-dioxo-4-[2-(3-methylureido)-ethyl]-1,4,5,6-tetrahydro-1,2,4-triazin-3-yl, 5,6-dioxo-4-[3-(3-methylureido)-propyl]-1,4,5,6-tetrahydro-1,2,4-triazin-3-yl, 5,6-dioxo-4-[2-(3-ethylureido)-ethyl]-1,4,5,6-tetrahydro-1,2,4-triazin-3-yl, 4-[2-(3,3-dimethylureido)ethyl]-5,6-dioxo-1,4,5,6-tetrahydro-1,2,4-triazin-3-yl, 4-[3-(3,3-dimethylureido)-propyl]-5,6-dioxo-1,4,5,6-tetrahydro-1,2,4-triazin-3-yl, 4-[2-(3,3-diethylureido)ethyl]-5,6-dioxo-1,4,5,6-tetrahydro-1,2,4-triazin-3-yl, 4-(2,2-dimethoxypropyl)-5,6-dioxo-1,4,5,6-tetrahydro-1,2,4-triazin-3-yl, 4-(3,3-dimethoxy-2-hydroxypropyl)-5,6-dioxo-1,4,5,6-tetrahydro-1,2,4-triazin-3-yl, 5,6-dioxo-4-[3-(dioxolan-2-yl)-2-hydroxypropyl]-1,4,5,6-tetrahydro-1,2,4-triazin-3-yl, 1-(2,2-dimethoxyethyl)-1,3,4-triazol-5-yl, 1-(3,3-dimethoxypropyl)-1,3,4-triazol-5-yl, 1-carbamoylmethyl-1,3,4-triazol-5-yl, 1-(2-hydroxyethyl)-1,3,4-triazol-5-yl, 1-(2-carbamoyloxyethyl)-1,3,4-triazol-5-yl, 1-(2-N-t-butoxycarbonylglycyloxyethyl)-1,3,4-triazol-5-yl, 1-(2-acetamidoethyl)-1,3,4-triazol-5-yl, 1-methylcarbamoylmethyl-1,3,4-triazol-5-yl, 1-dimethylcarbamoylmethyl-1,3,4-triazol-5-yl, 1-(2-dimethylcarbamoylethyl)-1,3,4-triazol-5-yl, 1-(2,2-dimethoxypropyl)-1,3,4-triazol-5-yl, 1-(2,2-dimethyldioxolan-4-yl)-methyl-1,3,4-triazol-5-yl, 1-(2,2-dimethyldioxan-5-yl)-1,3,4-triazol-5-yl, 1-(2-t-butoxycarbonylaminoethyl)-1,3,4-triazol-5-yl, 1-[2-(N-t-butoxycarbonyl-N-methylamino)-ethyl]-1,3,4-triazol-5-yl, 1-(2-dimethylaminoethyl)-1,3,4-triazol-5-yl, 1-(2-methylsulphonylaminoethyl)-1,3,4-triazol-5-yl, 1-(2-sulphamoylaminoethyl)-1,3,4-triazol-5-yl, 1-(2-glycoloylaminoethyl)-1,3,4-triazol-5-yl, 1-[2-(N-t-butoxycarbonylglycyl)-aminoethyl]-1,3,4-triazol-5-yl, 1-(2-methoxycarbonylaminoethyl)-1,3,4-triazol-5-yl, 1-(2-ureidoethyl)-1,3,4-triazol-5-yl, 1-[2-(3-methylureido)ethyl]-1,3,4-triazol-5-yl, 1-[2-(3,3-dimethylureido)ethyl]-1,3,4-triazol-5-yl, 1-(3,3-dimethoxy-2-hydroxypropyl)-1,3,4-triazol-5-yl, 1-(2-hydroxyethyl)-2-methoxycarbonyl-1,3,4-triazol-5-yl, 1-carbamoylmethyl-2-methoxycarbonyl-1,3,4-triazol-5-yl, 1-(2-carbamoylethyl)-2-methoxycarbonyl-1,3,4-triazol-5-yl, 1-(2-acetamidoethyl)-2-methoxycarbonyl-1,3,4-triazol-5-yl, 1-(2,2-dimethoxyethyl)-2-methoxycarbonyl-1,3,4-triazol-5-yl, 1-(dimethylcarbamoylmethyl)-2-methoxycarbonyl-1,3,4-triazol-5-yl, 1-(2,2-dimethyldioxolan-4-yl)-methyl-2-methoxycarbonyl-1,3,4-triazol-5-yl, 1-(2,2-dimethyldioxan-5-yl)-2-methoxycarbonyl-1,3,4-triazol-5-yl, 1-[2-(dioxolan-2-yl)-2-hydroxyethyl]-2-methoxycarbonyl-1,3,4-triazol-5-yl, 1-(2-dimethylaminoethyl)-2-methoxycarbonyl-1,3,4-triazol-5-yl, 2-methoxycarbonyl-1-(2-methylsulphonylaminoethyl)-1,3,4-triazol-5-yl, 2-methoxycarbonyl-1-(2-sulphamoylaminoethyl)-1,3,4-triazol-5-yl, 2-methoxycarbonyl-1-(2-methoxycarbonylaminoethyl)-1,3,4-triazol-5-yl, 2-methoxycarbonyl-1-(2-ureidoethyl)-1,3,4-triazol-5-yl, 2-methoxycarbonyl-1-[2-(3-methylureido)-ethyl]-1,3,4-triazol-5-yl, 1-[2-(3,3-dimethylureido)-ethyl]-2-methoxycarbonyl-1,3,4-triazol-5-yl, 1-(3,3-dimethoxy-2-hydroxypropyl)-2-methoxycarbonyl-1,3,4-triazol-5-yl, 1,4-dimethyl-5,6-dioxo-1,4,5,6-tetrahydro-1,2,4-triazin-3-yl, 1,4-diethyl-5,6-dioxo-1,4,5,6-tetrahydro-1,2,4-triazin-3-yl, 1-ethyl-4-methyl-5,6-dioxo-1,4,5,6-tetrahydro-1,2,4-triazin-3-yl, 4-ethyl-1-methyl-5,6-dioxo-1,4,5,6-tetrahydro-1,2,4-triazin-3-yl, 1-methyl-5,6-dioxo-1,4,5,6-tetrahydro-1,2,4-triazin-3-yl, 1-ethyl-5,6-dioxo-1,4,5,6-tetrahydro-1,2,4-triazin-3-yl, 2-methyl-5,6-dioxo-1,2,5,6-tetrahydro-1,2,4-triazin-3-yl, 2-ethyl-5,6-dioxo-1,2,5,6-tetrahydro-1,2,4-triazin-3-yl, 1-methyl-1,2,4-triazol-5-yl, 1-methyl-3-methoxycarbonyl-1,2,4-triazol-5-yl, 3-methoxycarbonyl-1-ethyl-1,2,4-triazol-5-yl, 1-methyl-3-ethoxycarbonyl-1,2,4-triazol-5-yl, 1-ethyl-3-ethoxycarbonyl-1,2,4-triazol-5-yl, 1,2,3-triazol-5-yl, 1,3,4-triazol-5-yl, 1,3,4-thiadiazol-5-yl, 2-methyl-1,3,4-thiadiazol-5-yl, 2-ethyl-1,3,4-thiadiazol-5-yl, 2-propyl-1,3,4-thiadiazol-5-yl, 2-isopropyl-1,3,4-thiadiazol-5-yl, 2-butyl-1,3,4-thiadiazol-5-yl, 2-isobutyl-1,3,4-thiadiazol-5-yl, 2-sec.-butyl-1,3,4-thiadiazol-5-yl, 2-t-butyl-1,3,4-thiadiazol-5-yl, 2-hydroxymethyl-1,3,4-thiadiazol-5-yl, 2-(2-hydroxyethyl)-1,3,4-thiadiazol-5-yl, 2-t-butoxycarbonylaminomethyl-1,3,4-thiadiazol-5-yl, 2-methyl-t-butoxycarbonylaminomethyl-1,3,4-thiadiazol-5-yl, 2-dimethylaminomethyl-1,3,4-thiadiazol-5-yl, 2-(2-t-butoxycarbonylaminoethyl)-1,3,4-thiadiazol-5-yl, 2-(2-methyl-t-butoxycarbonylaminoethyl)-1,3,4-thiadiazol-5-yl, 2-(2-dimethylaminoethyl)-1,3,4-thiadiazol-5-yl, 2-carboxymethyl-1,3,4-thiadiazol-5-yl, 2-(2-carboxyethyl)-1,3,4-thiadiazol-5-yl, 2-methoxy-1,3,4-thiadiazol-5-yl, 2-methylthio-1,3,4-thiadiazol-5-yl, 2-methylsulphonyl-1,3,4-thiadiazol-5-yl, 2-t-butoxycarbonylamino-1,3,4-thiadiazol-5-yl, 2-methyl-t-butoxycarbonylamino-1,3,4-thiadiazol-5-yl, 2-dimethylamino-1,3,4-thiadiazol-5-yl, 2-acetylamino-1,3,4-thiadiazol-5-yl, 2-hydroxy-1,3,4-thiadiazol-5-yl, 2-acetamidomethyl-1,3,4-thiadiazol-5-yl, 2-(2-acetamidoethyl)-1,3,4-thiadiazol-5-yl, 2-(2-hydroxyethylthio)-1,3,4-thiadiazol-5-yl, 3-methyl-1,2,4-thiadiazol-5-yl, 3-ethyl-1,2,4-thiadiazol-5-yl, 3-methoxy-1,2,4-thiadiazol-5-yl, 1,3,4-oxadiazol-5-yl, 2-methyl-1,3,4-oxadiazol-5-yl, 2-phenyl-1,3,4-oxadiazol-5-yl, 2-t-butoxycarbonylaminomethyl-1,3,4-oxadiazol-5-yl, 2-acetamidomethyl-1,3,4-oxadiazol-5-yl, 2-dimethylaminomethyl-1,3,4-oxadiazol-5-yl, oxazol-2-yl, 4-methyloxazol-2-yl, 1H-tetrazol-5-yl, 1-methyltetrazol-5-yl, 1-ethyltetrazol-5-yl, 1-propyltetrazol-5-yl, 1-isopropyltetrazol-5-yl, 1-butyltetrazol-5-yl, 1-(2-hydroxyethyl)-tetrazol-5-yl, 1-(3-hydroxypropyl)-tetrazol-5-yl, 1-methoxymethyltetrazol-5-yl, 1-carboxymethyltetrazol-5-yl, 1-sulphomethyltetrazol-5-yl, 1-(2-methyl-t-butoxycarbonylaminoethyl)-tetrazol-5-yl, 1-(2-dimethylaminoethyl)-tetrazol-5-yl, 1-(2-diethylaminoethyl)-tetrazol-5-yl, 1-(3-dimethylaminopropyl)tetrazol-5-yl, 1-(2-sulphamoylaminoethyl)-tetrazol-5-yl, 1-(2-acetamidoethyl)-tetrazol-5-yl, 1-sulphamoylmethyltetrazol-5-yl, 1-(2-carboxymethylaminoethyl)-tetrazol-5-yl, 1-(2-sulphoaminoethyl)-tetrazol-5-yl, 1-(2-ureidoethyl)-tetrazol-5-yl, 1-[2-(3-methylureido)-ethyl]tetrazol-5-yl, 1-[2-(3,3-dimethylureido)-ethyl]tetrazol-5-yl, 1-(2,2-dimethyldioxolan-4-yl)-methyltetrazol-5-yl, 1-(2,2-dimethyldioxan-5-yl)-tetrazol-5-yl, 1-(2,2-dimethoxyethyl)-tetrazol-5-yl, 1-(3,3-dimethoxypropyl)tetrazol-5-yl and 1-(dioxolan-2-yl-ethyl)-tetrazol-5-yl.

Amongst the meanings of the symbol R° representing an alkyl radical, the following may be mentioned: methyl, ethyl, propyl, isopropyl, butyl, isobutyl and sec.-butyl.

When R° represents a protecting radical, it can be selected from oxime-protecting radicals which are normally used, and the use of which does not adversely affect the rest of the molecule. It can represent, for example, a trityl, tetrahydropyranyl or 2-methoxyprop-2-yl radical.

In general, the syn forms of the compounds of general formula I are preferred.

According to a feature of the invention, the compounds of general formula I, wherein R is as hereinbefore defined, can be prepared by reacting an acid (or a reactive derivative of an acid) of the general formula:

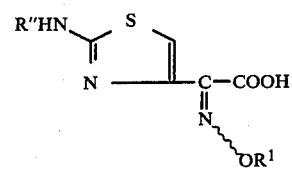

V (wherein $R^1$ is as hereinbefore defined for R° but does not represent a hydrogen atom and R″ is as hereinbefore defined for R′, except that it does not represent the hydrogen atom, or, if the reactive derivative of the acid of general formula V is the acid chloride, R″ can represent a hydrogen atom) with a thiol of the general formula

R—SH        VI (wherein R is as hereinbefore defined) or with an alkali metal or alkaline earth metal salt thereof, and then removing the radical R″ protecting the amino radical, if it is desired to obtain a product in which R′ is a hydrogen atom, and, if appropriate, removing the other protecting radicals.

It is to be understood that use of the acid of general formula V in the syn or anti form, or mixtures thereof, in the process of the invention leads respectively to the compounds of general formula I in the syn or anti form, or to mixtures thereof.

If it is desired to obtain a compound of general formula I wherein R° is a hydrogen atom, the protection of the oxime can be carried out by any known method which does not adversely affect the rest of the molecule. The trityl group is particularly preferred.

By the expression "known methods" as used in this specification is meant methods heretofore used or described in the chemical literature.

If it is desired to obtain a compound of general formula I wherein R contains a carboxy or sulpho radical, it is preferable to use a reactive derivative of the acid of general formula V in the reaction with the corresponding thiol.

If it is desired to obtain a compound of general formula I wherein R contains a hydroxy radical, it is preferable to protect this radical beforehand by a trityl group.

A. If the compound of general formula V is used in the form of the acid, the condensation is generally carried out in an organic solvent, such as dimethylformamide, acetonitrile, tetrahydrofuran, methylene chloride, chloroform or ethyl acetate, in the presence of a condensation agent, such as a carbodiimide (e.g. dicyclohexylcarbodiimide), N,N'-carbonyldiimidazole or 2-ethoxy-1-ethoxycarbonyl-1,2-dihydroquinoline, at a temperature from $-20°$ to $40°$ C., and the protecting groups are then removed, if appropriate.

B. If a reactive derivative of the acid of general formula V is used, it is possible to employ the anhydride, a mixed anhydride or a reactive ester of the general formula

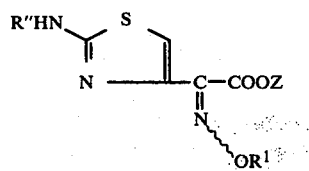

wherein $R^1$ and $R''$ are as hereinbefore defined and Z represents a radical such as succinimido, benzotriazol-1-yl, 4-nitrophenyl, 2,4-dinitrophenyl, pentachlorophenyl or phthalimido.

C. If it is desired to obtain a compound of general formula I wherein R' is a hydrogen atom, it is also possible to use an acid halide, e.g. the acid chloride, the hydrochloride of the chloride of the acid of the general formula V being reacted with the thiol of general formula VI or with one of its salts.

If the anhydride, a mixed anhydride or an acid halide (which can all be prepared in situ) is used, the condensation is carried out in an inert organic solvent, such as an ether (e.g. tetrahydrofuran or dioxan), a chlorinated hydrocarbon solvent (e.g. chloroform or methylene chloride), an amide (e.g. dimethylformamide or dimethylacetamide) or a ketone (e.g. acetone), or a mixture of the above solvents, in the presence of an acid acceptor, such as an epoxide (e.g. propylene oxide) or such as a nitrogen-containing organic base e.g. pyridine, N-methylmorpholine or a trialkylamine (e.g. triethylamine), or in an aqueous-organic medium, in the presence of an alkaline condensation agent, such as sodium bicarbonate, the reaction being carried out at a temperature from $-40°$ to $+40°$ C., and the protecting group or groups are then removed, if appropriate.

If a reactive ester of general formula VII is used, the reaction is generally carried out in the presence of a trialkylamine (e.g. triethylamine), in an organic solvent, such as dimethylformamide, at a temperature from $0°$ to $60°$ C., and the protecting group or groups are then removed, if appropriate.

By way of example, the freeing of the various protected radicals can be carried out under the following conditions:

if it is desired to obtain a compound of general formula I wherein R' is hydrogen, a t-butoxycarbonyl radical protecting the aminothiazole is removed by treatment in an anhydrous acid medium. In this case, the product is obtained either in the form of a salt or in the form of a solvate with the acid employed. Preferably, trifluoroacetic acid is used, the reaction being carried out at from $0°$ to $20°$ C. It is also possible to use catalytic hydrogenation to remove a benzyl radical protecting the aminothiazole;

if it is desired to obtain a compound of general formula I wherein the radical R contains a hydroxy group and/or in which $R°$ is a hydrogen atom, a trityl group or groups are removed by acidolysis with anhydrous trifluoroacetic acid. The removal is carried out before, simultaneously with or after the removal of a radical protecting the aminothiazole.

According to a further feature of the invention, the thioloesters of general formula I wherein R contains a carbamoyloxyalkyl or acyloxyalkyl substituent (the acyl moiety of acyloxyalkyl being optionally substituted by a protected amino or alkylamino radical or a dialkylamino radical), can be prepared from a thioloester of the general formula:

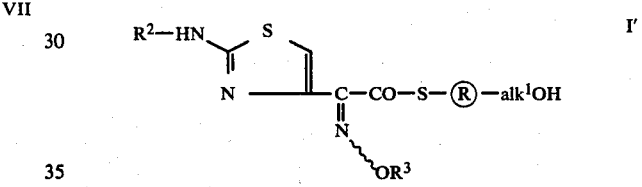

wherein the radical $R^2$ is as hereinbefore defined for R' but does not represent a hydrogen atom, the radical $R^3$ is as hereinbefore defined for $R°$ but does not represent a hydrogen atom and — ⓡ —alk$^1$OH represents a radical ⓡ containing a hydroxyalkyl substituent, by any known method for obtaining a carbamate or an ester from an alcohol without affecting the rest of the molecule.

The esterification of the group — R —alk$^1$OH is carried out at a temperature from $-50°$ C. to the reflux temperature of the reaction mixture, in particular by condensing the anhydride of the acid (or another reactive derivative, e.g. a halide), in an inert organic solvent, such as an ether (e.g. tetrahydrofuran), a chlorinated hydrocarbon solvent (e.g. methylene chloride) or a mixture of these solvents, in the presence of a nitrogen-containing base, such as pyridine, 4-dimethylaminopyridine or a trialkylamine (e.g. triethylamine), or in the presence of an alkaline condensation agent (e.g. sodium bicarbonate), and the protecting groups are then removed, if appropriate, in accordance with the methods described above.

The carbamate is prepared from the group — ⓡ —alk$^1$OH by any known method which does not adversely affect the rest of the molecule. This is done, in particular, by reaction with chlorosulphonyl or trichloroacetyl isocyanate, in an inert organic solvent, e.g. tetrahydrofuran or acetonitrile, at a temperature between $-80°$ and $20°$ C., followed by treatment with a base (e.g. an alkali metal bicarbonate or sodium hydroxide), in an aqueous medium, and then removal of the protecting groups.

The acids of general formula V wherein $R^1$ is hydrogen, alkyl or trityl can be prepared in accordance with the method described in Belgian Pat. No. 850,662.

The acids of general formula V wherein $R^1$ is a vinyl radical can be prepared in accordance with the method described in Belgian Pat. No. 869,079.

The acids of general formula V wherein $R^1$ is a cyanomethyl radical can be prepared in accordance with the method described in published German Patent Application No. 2,812,625.

The acids of general formula V wherein $R^1$ is a protecting radical can be prepared by protecting the oxime of the particular acid, in which $R^1$ is hydrogen, by any known method which does not adversely affect the rest of the molecule.

The thiols of general formula VI (which can be used in their tautomeric form) can be prepared by applying one of the following methods, depending on the meaning of the radical R:

if R is a pyrid-3-yl radical: in accordance with the method described by H. M. Wuest and E. H. Sakal, J. Amer. Chem. Soc., 73, 1,210 (1951).

if R is a pyrid-3-yl-1-oxide radical: in accordance with the method described by B. Blank et al., J. Med. Chem., 17, 1,065 (1974).

if R is a pyrid-4-yl-1-oxide radical: in accordance with the method described by R. A. Y. Jones et al., J. Chem. Soc., 2,937 (1960).

if R is a pyridazin-3-yl radical substituted by alkyl or methoxy and optionally N-oxidised: in accordance with the method described in Belgian Pat. No. 787,635.

if R is a pyridazin-3-yl radical substituted by amino and optionally N-oxidised: in accordance with the method described in Belgian Pat. No. 579,291.

if R is a pyridazin-3-yl radical substituted by acylamino and optionally N-oxidised: by applying the methods described by M. Kumagai and M. Bando, Nippon Kagaku Zasshi, 84, 995 (1963), and by T. Horie and T. Ueda, Chem. Pharm. Bull., 11, 114 (1963).

if R is a tetrazolo[4,5-b]pyridazin-6-yl radical: in accordance with the method described in Belgian Pat. No. 804,251.

If R is a 5,6-dioxo-1,4,5,6-tetrahydro-1,2,4-triazin-3-yl radical substituted in the 4-position, or a 2-alkoxycarbonyl-1,3,4-triazol-5-yl radical substituted in the 1-position, by a radical $R^\gamma$ chosen from amongst:

(a) an allyl radical, or an alkyl radical (containing 1 to 4 carbon atoms and itself optionally substituted by an alkoxy, alkylthio, phenyl, carbamoyl, alkylcarbamoyl, dialkylcarbamoyl, acyl, alkoxycarbonyl or thiazolidin-2-yl radical), (b) a 2,3-dihydroxypropyl or 1,3-dihydroxyprop-2-yl radical (optionally protected in the form of a cyclic acetal), (c) an alkyl radical (containing 2 to 4 carbon atoms and itself substituted by hydroxy, carbamoyloxy, dialkylamino, alkylsulphinyl, alkylsulphonyl, alkylsulphonylamino, sulphamoylamino, acylamino (optionally substituted), alkoxycarbonylamino, ureido, alkylureido or dialkylureido), (d) a radical of general formula II or III, and (e) a hydroxyiminoalkyl or alkoxyiminoalkyl radical: by reacting an alkyl oxalate with a thiosemicarbazide of the general formula:

  VIII (wherein $R^\gamma$ is as hereinbefore defined), in the presence of an alkali metal alkoxide, e.g. sodium ethoxide or methoxide or potassium t-butoxide, by applying the method described by M. Pesson and M. Antoine, Bull. Soc. Chim. France, (1970), 1,590.

It is not absolutely necessary to purify the product obtained (or to free the protected radicals) in order to use it for the preparation of the compounds of the general formula I.

The thiosemicarbazide of general formula VIII can be prepared in accordance with one of the methods described by K. A. Jensen et al., Acta. Chem. Scand., 22, 1 (1968), or by applying the method described by Y. Kazakov and J. Y. Potovskii, Doklady Acad. Nauk, SSSR, 134, 824 (1960), it being understood that, if $R^\gamma$ contains an amino radical, the latter is protected.

The protection of the amino radical and the removal of the protecting radical are carried out in accordance with known methods which do not adversely affect the rest of the molecule. The t-butoxycarbonyl group, which can be removed by acid hydrolysis, is preferred.

If R is a 1,3,4-triazol-5-yl radical substituted in the 1-position by an alkyl, allyl or alkoxyalkyl radical, by an alkyl radical (containing 1 to 4 carbon atoms) which is itself substituted as just defined above under (a), with the exception of a thiazolidin-2-yl radical, by a radical as just defined above under (c) or by an alkoxyiminoalkyl radical: by applying one of the methods described by M. Pesson and M. Antoine, Bull. Soc. Chim. France, 1,590 (1970).

If R is a 1,3,4-triazol-5-yl radical substituted in the 1-position by thiazolidin-2-yl-alkyl or hydroxyiminoalkyl: by reacting cysteamine or hydroxylamine, respectively, with a 1-dialkoxyalkyl-5-mercapto-1,3,4-triazole, which can be obtained from a 4-dialkoxyalkylthiosemicarbazide by applying the method described by M. Kanaoka, J. Pharm. Soc. Japan, 75, 1,149 (1955).

If R is a 1,3,4-triazol-5-yl radical substituted in the 1-position by 2,3-dihydroxypropyl or 1,3-dihydroxyprop-2-yl (optionally protected in the form of a cyclic acetal) or represents a radical of general formula II or III: by applying the method described by M. Kanaoka, J. Pharm. Soc. Japan, 75, 1,149 (1955).

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by acyloxyalkyl (optionally substituted): by respectively acylating 5,6-dioxo-4-hydroxyalkyl-3-mercapto-1,4,5,6-tetrahydro-1,2,4-triazine, 2-alkoxycarbonyl-1-hydroxyalkyl-5-mercapto-1,3,4-triazole or 1-hydroxyalkyl-5-mercapto-1,3,4-triazole, in which the mercapto radical has been protected beforehand (e.g. according to C. G. Kruse et al., Tet. Lett., 1,725 (1976)), by any known method for acylating an alcohol without affecting the rest of the molecule, and then freeing the mercapto group in an acid medium.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by aminoalkyl or alkylaminoalkyl: by freeing the amine group of the corresponding product protected e.g. by a t-butoxycarbonyl group.

If R is a 5,6-dioxo-1,4,5,6-tetrahydro-1,2,4-triazin-3-yl radical substituted in the 4-position, or a 2-alkoxycarbonyl-1,3,4-triazol-5-yl or 1,3,4-triazol-5-yl radical substituted in the 1-position, by sulphoaminoalkyl: from the corresponding product substituted by a t-butoxycarbonylaminoalkyl radical, by analogy with the method described in Belgian Pat. No. 847,237.

If R is a 1,4-dialkyl-1,4,5,6-tetrahydro-1,2,4-triazin-3-yl or 1-alkyl-5,6-dioxo-1,4,5,6-tetrahydro-1,2,4-triazin-3-yl radical: in accordance with the method described in Belgian Pat. No. 830,455.

If R is a 2-alkyl-5,6-dioxo-1,2,5,6-tetrahydro-1,2,4-triazin-3-yl or 1-alkyl-3-alkoxycarbonyl-1,2,4-triazol-5-yl radical: in accordance with the method described by M. Pesson and M. Antoine, C. R. Acad. Sci., Ser. C, 267, 25, 1,726 (1968).

If R is a 1,2,3-triazol-5-yl radical: in accordance with the method described in published French Patent Application 2,215,942.

If R is a 1,3,4-triazol-5-yl radical: in accordance with the method described by M. Kanaoka, J. Pharm. Soc. Jap., 75, 1,149 (1955).

If R is a 1,3,4-thiadiazol-5-yl radical optionally substituted by alkyl, alkoxy, alkylthio, alkylsulphonyl, amino, alkylamino, dialkylamino or acylamino: in accordance with the methods described in Belgian Pat. No. 830,821.

If R is a 1,3,4-thiadiazol-5-yl radical substituted by hydroxyalkyl, aminoalkyl, alkylaminoalkyl or dialkylaminoalkyl: in accordance with the method described in published German Patent Application No. 2,446,254.

If R is a 1,3,4-thiadiazol-5-yl radical substituted by a carboxyalkyl radical: by applying the method described in published German Patent Application No. 1,953,861.

If R is a 1,3,4-thiadiazol-5-yl radical substituted by a trifluoromethyl radical: in accordance with the method described in published German Patent Application No. 2,162,575.

If R is a 1,3,4-thiadiazol-5-yl radical substituted by a carboxyl radical: in accordance with the method described in published Japanese Patent Application No. 77/48,666.

If R is a 1,3,4-thiadiazol-5-yl radical substituted by an acylaminoalkyl radical: in accordance with the method described in published Japanese Patent Application No. 76/80,857.

If R is a 1,3,4-thiadiazol-5-yl radical substituted by a hydroxyalkylthio radical: by applying the method described by G. Nannini, Arz. Forsch., 27 (2), 343 (1977).

If R is a 1,2,4-thiadiazol-5-yl radical substituted by alkyl or alkoxy: in accordance with the method described in published German Patent Application 2,806,226 or according to Chem. Ber., 90, 184 (1957).

If R is a 1,3,4-oxadiazol-5-yl radical as defined above under 8 (a): by applying the method described by E. Hoggarth, J. Chem. Soc., 4,811 (1952).

If R is an oxazol-2-yl or 4-alkyloxazol-2-yl radical: by applying the method previously described by C. Bradsher, J. Org. Chem., 32, 2,079 (1967).

If R is a tetrazol-5-yl radical optionally substituted in the 1-position by alkyl, hydroxyalkyl or phenyl: in accordance with the methods described in Belgian Pat. No. 830,821.

If R is a tetrazol-5-yl radical substituted in the 1-position by alkoxyalkyl: by adding sodium azide to an isothiocyanatoalkoxyalkyl compound, the reaction being carried out in an organic solvent, such as ethanol, at the reflux temperature of the reaction mixture.

The isothiocyanatoalkoxyalkyl compound can be obtained by applying the method described by E. Schmidt et al., Chem. Ber., 73, 286 (1940).

If R is a tetrazol-5-yl radical substituted in the 1-position by a carboxyalkyl radical: in accordance with the method described in Belgian Pat. No. 858,112.

If R is a tetrazol-5-yl radical substituted in the 1-position by a sulphoalkyl radical: in accordance with the method described in Belgian Pat. No. 856,498 or described by D. A. Berges et al., J. Het. Chem., 15, 981 (1978).

If R is a tetrazol-5-yl radical substituted in the 1-position by an aminoalkyl, alkylaminoalkyl or dialkylaminoalkyl radical: by applying the method described in published German Patent Application No. 2,738,711.

If R is a tetrazol-5-yl radical substituted in the 1-position by a sulphamoylalkyl, sulphamoylaminoalkyl or sulphoaminoalkyl radical: in accordance with the method described in Belgian Pat. No. 856,636.

If R is a tetrazol-5-yl radical substituted by an acylaminoalkyl radical or a 1,3,4-thiadiazol-5-yl radical substituted by hydroxy: in accordance with the method described in U.S. Pat. No. 4,117,123.

If R is a tetrazol-5-yl radical substituted in the 1-position by a ureidoalkyl, alkylureidoalkyl or dialkylureidoalkyl radical: from the corresponding product substituted by aminoalkyl (and in which the mercapto radical has been protected beforehand), by treatment with an alkali metal isocyanate, with an alkyl isocyanate or with a dialkylcarbamoyl halide, followed by freeing of the mercapto group under the conditions described in Belgian Pat. No. 847,237.

If R is a tetrazol-5-yl radical substituted in the 1-position by a carboxyalkylaminoalkyl radical: in accordance with the method described in published German Patent Application No. 2,715,597.

If R is a tetrazol-5-yl radical substituted in the 1-position by a 2,3-dihydroxypropyl radical: in accordance with the method described in U.S. Pat. No. 4,064,242.

If R is a tetrazol-5-yl radical substituted in the 1-position by a 1,3-dihydroxyprop-2-yl radical: by reacting sodium azide with a 2,2-dimethyl-1,3-dioxolan-5-yl isothiocyanate (and then freeing the hydroxy groups, if appropriate).

If R is a tetrazol-5-yl radical substituted in the 1-position by a radical of general formula II as defined above under (9e), or of the general formula III, or a radical defined above under (9c): by reacting sodium azide with the corresponding isothiocyanate, by analogy with the method described by R. E. Orth, J. Pharm. Sci., 52 (9), 909 (1963), it being understood that, in the case where R contains a hydroxy or hydroxyiminoalkyl substituent, the alcohol or the oxime is optionally protected, e.g. by a tetrahydropyranyl group.

The compounds of general formula I are useful for the preparation of cephalosporins of the general formula

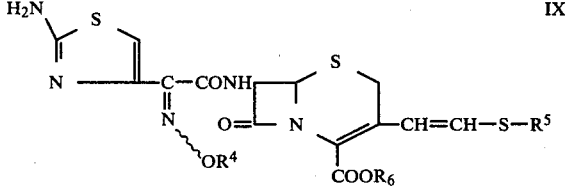

wherein the symbol $R^4$ represents a hydrogen atom or an alkyl, cyanomethyl or vinyl radical, the symbol $R^5$ is chosen from amongst the meanings given above for R in general formula I, it being understood that the amino, alkylamino, carboxy or hydroxy substituents are free, or $R^5$ represents a 5,6-dioxo-1,4,5,6-tetrahydro-1,2,4-triazin-3-yl radical substituted in the 4-position, a 1,3,4- triazol-5-yl or 2-alkoxycarbonyl-1,3,4-triazol-5-yl radical substituted in the 1-position, or a tetrazol-5-yl radical substituted in the 1-position, by a formylalkyl or 2-formyl-2-hydroxyethyl radical, and the symbol $R^6$ represents a hydrogen atom or a radical which can easily be removed enzymatically, of the general formula

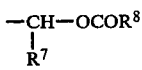    X wherein $R^7$ represents a hydrogen atom or an alkyl radical and $R^8$ represents an alkyl radical or the cyclohexyl radical.

In general formula IX, the substituent in the 3-position can be in the cis or trans form or in the form of a mixture of the cis and trans forms. In the following text, the trans stereoisomer will be denoted by E and the cis stereoisomer will be denoted by Z.

The compounds of general formula IX can be prepared in the following manner:

A compound of general formula I, optionally in the form of a salt, is reacted with a 7-aminocephalosporin (or, if appropriate, with a mixture of the isomers thereof) of the general formula

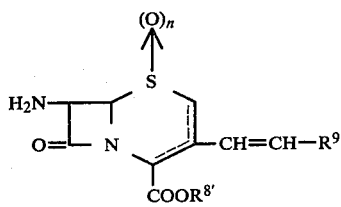    XI wherein n is 0 or 1 (if n=0, the product is in the form of a bicyclooct-2-ene or -3-ene, and if n=1, the product is in the form of a bicyclooct-2-ene (according to the nomenclature of Chemical Abstracts)), the substituent on the carbon atom in the 3-position of the bicyclooctene exhibits E/Z stereoisomerism, $R^{8'}$ represents a hydrogen atom, a radical of general formula X or a protecting radical which can easily be removed (e.g. methoxymethyl, t-butyl, benzhydryl, p-nitrobenzyl or p-methoxybenzyl) and $R^9$ represents a radical of the general formula:

    XII or

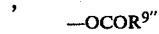    XIII (wherein $R^{9'}$ is an alkyl, trifluoromethyl or trichloromethyl radical or a phenyl radical which is optionally substituted (by a halogen atom or by an alkyl or nitro radical) and $R^{9''}$ is as defined for $R^{9'}$ or represents acylmethyl, 2-acylethyl, 2-acylpropyl, alkoxycarbonylmethyl, 2-alkoxycarbonylethyl or 2-alkoxycarbonylpropyl), and the sulphoxide obtained (if n=1) is then reduced, if appropriate, and the protecting radicals are removed, if appropriate.

It is to be understood that, if the radical R in the compound of general formula I is capable of interfering with the reaction, it is preferable to protect this radical under the conditions described above (in particular if R contains a hydroxy or carboxy radical).

If a compound of general formula I in which R' and/or R° represents a hydrogen atom is used, it is necessary to protect the amine and/or the oxime groupings.

If it is desired to obtain a compound of general formula IX in which $R^5$ contains a formylalkyl or acylalkyl radical, the corresponding compound in which the formylalkyl or acylalkyl radical is protected in the form of an acetal (in the form of a radical of general formula II or III) is prepared, and the protecting group is then removed before, after or simultaneously with the other protecting groups present in the molecule, by any known method of deacetalisation which does not adversely affect the rest of the molecule.

The removal of the protecting radicals in the groups of general formula II or III (if it is desired to obtain a compound of general formula IX in which $R^5$ contains a formylalkyl or acylalkyl radical) is carried out:

in the presence of a sulphonic acid (e.g. methanesulphonic acid or p-toluenesulphonic acid), in an organic solvent (e.g. acetonitrile or acetone), optionally in the presence of water and optionally in the presence of a reactant which can be converted to an acetal, such as acetone, glyoxylic acid, benzaldehyde or pyruvic acid, at a temperature between 20° C. and the reflux temperature of the reaction mixture;

or alternatively, if the radical $R^5$ is a 5,6-dioxo-1,4,5,6-tetrahydro-B 1,2,4-triazin-3-yl radical substituted in the 4-position by a formylalkyl or acylalkyl radical, by reaction with aqueous formic acid (preferably containing less than 10% of water), either in the presence or absence of silica, or by transacetalisation in the presence of a reactant which can be converted to an acetal, for example as defined above.

If the radical $R^5$ in the compound of general formula IX contains a formylalkyl substituent, it can be in the form of the free aldehyde or the aldehyde hydrate.

It is understood that the thioloesters in the syn or anti form, or mixtures thereof, lead to the 3-thiovinylcephalosporins of general formula IX in the syn or anti form, or to mixtures thereof, respectively.

The reaction of the compounds of general formula I with the 7-aminocephalosporins of general formula XI is generally carried out in the presence of an acid acceptor, such as an organic base, and more particularly in the presence of a pyridine or a nitrogen-containing organic base of the general formula:

    XIV (wherein $X_1$, $Y_1$ and $Z_1$ represent alkyl or phenyl radicals or two of them form a ring with the nitrogen atom to which they are attached), for example, triethylamine, N,N-diisopropylethylamine, diethylphenylamine or N-methylmorpholine.

The reaction is advantageously carried out in an organic solvent, such as an amide (e.g. dimethylformamide or dimethylacetamide), an ether (e.g. tetrahydrofuran or dioxane), a chlorinated hydrocarbon solvent (e.g. chloroform or methylene chloride), a ketone (e.g. acetone) or a nitrile (e.g. acetonitrile), or alternatively in a mixture of these solvents.

It is also posible to carry out the reaction in the present of an alkali metal bicarbonate, in one of the above-mentioned solvents, optionally in the presence of water.

If a compound of general formula I in which R' and/or R° are hydrogen is used, it is preferable to protect the amine and/or the oxime beforehand.

The reaction is carried out at a temperature between −20° C. and the reflux temperature of the reaction mixture. It is optionally carried out under nitrogen.

The reduction of the S-oxide is carried out e.g. under the conditions described in published German Patent Application No. 2,637,176.

If it is desired to prepare a compound of general formula IX in which $R^5$ contains a hydroxy, sulpho, sulphinyl or sulphonyl substituent, it is preferable to use a compound of the general formula XI in which n=0.

The removal of the various protecting radicals can be carried out simultaneously or successively.

By way of example:

1. The removal of the radicals protecting amine groups is carried out:

in the case of a t-butoxycarbonyl, trityl, p-methoxybenzyloxycarbonyl or formyl radical: by treatment in an acid medium. Preferably, trifluoroacetic acid is used, the reaction being carried out at a temperature between 0° and 20° C.; alternatively anhydrous or aqueous formic acid is used, or also para-toluenesulphonic or methanesulphonic acid is used, in acetone or in acetonitrile, at 20° C. to the reflux temperature of the reaction mixture. Under these conditions, the compound of general formula I is obtained in the form of the trifluoroacetate, the solvate with formic acid, the methanesulphonate or the para-toluenesulphonate, in which the amine group can be freed by any known method for obtaining an amine from one of its salts without affecting the rest of the molecule. The reaction is carried out, in particular, by bringing the product into contact with an ion exchange resin or by reacting it with an organic base;

in the case of a 2,2,2-trichloroethoxycarbonyl or p-nitrobenzyloxycarbonyl radical: by reduction (in particular by treatment with zinc in acetic acid);

in the case of a chloroacetyl or trichloroacetyl radical: by applying the method described in the published French Pat. No. 2,243,199;

in the case of a benzyl, dibenzyl or benzyloxycarbonyl radical: by catalytic hydrogenation; or in the case of a trifluoroacetyl radical: by treatment in a basic medium.

2. The removal of the radicals protecting the carboxy group is carried out:

in the case of a t-butyl, p-methoxybenzyl or benzhydryl group: by treatment in an acid medium under the conditions described above for the removal of the trityl radical protecting amino (in the case of the benzhydryl radical, the reaction can be carried out in the presence of anisole);

in the case of a methoxymethyl group: by treatment in a dilute acid medium;

in the case of a p-nitrobenzyl group: by reduction (in particular by treatment with zinc in acetic acid or by hydrogenolysis);

3. The removal of radicals protecting the oxime and/or the hydroxy groups is carried out:

in the case of a trityl or tetrahydropyranyl group or 2,2-dimethyldioxolan-4-yl-methyl or 2,2-dimethyldioxan-5-yl radicals: by acidolysis, e.g. with trifluoroacetic acid, aqueous or non-aqueous formic acid or paratoluenesulphonic acid (if aqueous or non-aqueous formic acid is used, the freeing of the hydroxy radicals protected in the form of a cyclic acetal can lead, at least partially, to the corresponding monoformates or diformates, which can be separated by chromatography, if appropriate);

in the case of the 2-methoxyprop-2-yl group; in accordance with the method described in Belgian Pat. No. 875,379.

The compounds of general formula XI can be obtained from a compound, or a mixture of isomers, of the general formula:

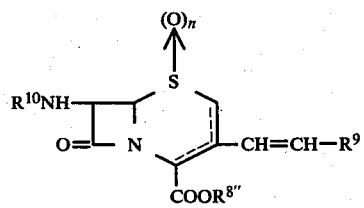

(wherein $R^9$ and n are as hereinbefore defined, the position of the double bond is as defined above for the compounds of general formula XI, $R^{8''}$ is as hereinbefore defined for $R^{8'}$, except that it does not represent the hydrogen atom, and $R^{10}$ is a radical which can easily be removed) by removing the radical $R^{10}$ or, if appropriate, simultaneously removing the radicals $R^{10}$ and $R^{8''}$ if it is desired to obtain a compound of general formula XI in which $R^{8'}$ is a hydrogen atom.

In the definition of the radical $R^{10}$ it is to be understood that the expression "a radical which can be easily removed" means a benzhydryl or trityl radical, a 2,2,2-trichloroethyl radical, an acyl radical of the general formula:

$$R^{11}-CO- \qquad \qquad XVI$$

[wherein $R^{11}$ represents a hydrogen atom, an alkyl radical (optionally substituted by one or more halogen atoms or by a phenyl or phenoxy radical) or a phenyl radical], or alternatively a radical of the general formula:

$$R^{12}OCO- \qquad \qquad XVII$$

wherein $R^{12}$ represents an unsubstituted branched alkyl radical, a linear or branched alkyl radical [carrying one or more substituents selected from halogen atoms, a cyano, trialkylsilyl or phenyl radical or a phenyl radical which is substituted (by one or more alkoxy, nitro or phenyl radicals)] or a vinyl, allyl or quinolyl radical or a nitrophenylthio radical. Furthermore, the radical $R^{10}NH$ can be replaced by a methyleneimino radical in which the methylene radical is substituted by a dialkylamino or aryl group (the latter being optionally substituted by one or more methoxy or nitro radicals).

The following radicals may be mentioned as examples of radicals $R^{10}$ which can be used: formyl, acetyl, chloroacetyl, trichloroacetyl, phenylacetyl, phenoxyacetyl, benozyl, t-butoxycarbonyl, 2-chloro-1,1-dimethylethoxycarbonyl, 2,2,2-trichloroethoxycarbonyl, 2,2,2-trichloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio and p-nitrophenylthio.

The following may be mentioned as examples of methyleneimino radicals: dimethylaminomethyleneimino, 3,4-dimethoxybenzylideneimino and 4-nitrobenzylideneimino.

The removal of the radical $R^{10}$ is carried out by any known method for freeing an amine group without affecting the rest of the molecule.

The following methods may be mentioned by way of example:

if $R^{10}$ represents trityl, benzhydryl, trichloroacetyl, chloroacetyl, t-butoxycarbonyl, trichloroethoxycarbonyl, benzyloxycarbonyl, p-methoxybenzyloxycarbonyl or p-nitrobenzyloxycarbonyl: in accordance with the abovementioned method for freeing the amino radical of the compound of general formula IX;

if $R^{10}$ represents formyl, 2-chloro-1,1-dimethylethoxycarbonyl, 2-cyano-1,1-dimethylethoxycarbonyl, 3,5-dimethoxybenzyloxycarbonyl, diphenylmethoxycarbonyl, 2-(biphenyl-4-yl)-isopropoxycarbonyl, vinyloxycarbonyl, allyloxycarbonyl, quinol-8-yl-oxycarbonyl, o-nitrophenylthio or p-nitrophenylthio, and if $R^{10}NH$ is replaced by dimethylaminomethyleneimino, 3,4-dimethoxybenzylideneimino or 4-nitrobenzylideneimino: by hydrolysis in an acid medium;

if $R^{10}$ represents 2,2,2-trichloroethoxycarbonyl or 2,2,2-trichloro-1,1-dimethylethoxycarbonyl: by treatment with zinc in acetic acid;

if $R^{10}$ represents acetyl, benzoyl, phenylacetyl or phenoxyacetyl: in accordance with the method described in Belgian Patent 758,800;

if $R^{10}$ represents trimethylsilylethoxycarbonyl: in accordance with the method described by H. Gerlach, Helv. Chim. Acta, 60 (8), 3,039 (1977); and if $R^{10}$ represents p-nitrobenzyloxycarbonyl: by hydrogenolysis in the presence of palladium.

The compounds of general formula XV can be prepared by reacting an activated derivative of the acids $R^{9'}SO_3H$ and $R^{9''}COOH$, of the following type:

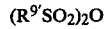  (R$^{9'}$SO$_2$)$_2$O    XVIII

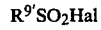  R$^{9'}$SO$_2$Hal    XIX

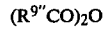  (R$^{9''}$CO)$_2$O    XX

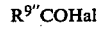  R$^{9''}$COHal    XXI (wherein $R^{9'}$ and $R^{9''}$ are as hereinbefore defined and Hal represents a halogen atom) with a compound (or a mixture of the isomers) of the general formula:

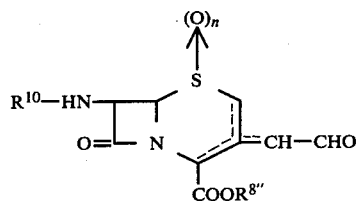

(wherein $R^{8''}$, $R^{10}$ and n are as hereinbefore defined, it being understood that, if n=0, the product is in the form of a bicyclooct-2-ene or -3-ene or a 3-oxoethylidenebicyclooctane, and if n=1, the product is in the form of a bicyclooct-2-ene or a 3-oxoethylidenebicyclooctane) and then, if appropriate, reducing the sulphoxide obtained if it is desired to prepare a compound of general formula XV in which n=0 from a compound of general formula XXII in which n=1.

The reaction is generally carried out in the presence of a tertiary base, such as defined by general formula XIV, e.g. triethylamine or N,N-dimethylaniline, in a chlorinated organic solvent (e.g. methylene chloride), in an ester (e.g. ethyl acetate), in an ether (e.g. dioxan or tetrahydrofuran), in an amide (e.g. dimethylacetamide or dimethylformamide), in acetonitrile or in N-methylpyrrolidone, or directly in a basic solvent, such as pyridine, or alternatively the reaction is carried out in an aqueous-organic medium, in the presence of an alkaline condensation agent (i.e. an alkali metal bicarbonate, sodium hydroxide or potassium hydroxide), at a temperature between $-78°$ C. and the reflux temperature of the reaction mixture. The reaction is optionally carried out under a nitrogen atmosphere.

It is not absolutely necessary, in order to carry out this reaction, to have purified the intermediate of general formula XXII.

The compounds of general formula XXII in which n is equal to 0 can be obtained by hydrolysing the enamine (or the mixture of isomeric enamines) of the general formula:

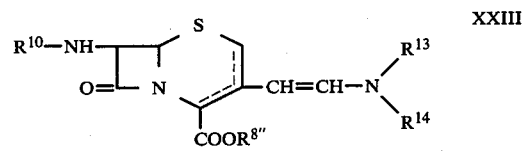

wherein $R^{8''}$ and $R^{10}$ are as hereinbefore defined, the product is in the form of a bicyclooct-2-ene or -3-ene, the substituent on the carbon atom in the 3-position of the bicyclooctene exhibits E/Z stereoisomerism and $R^{13}$ and $R^{14}$, which are identical or different, represent alkyl radicals (optionally substituted by a hydroxy, alkoxy, amino, alkylamino or dialkylamino radical) or phenyl radicals or form, together with the nitrogen atom to which they are attached, a saturated 5- or 6-membered heterocyclic ring which optionally contains another hetero-atom selected from nitrogen, oxygen or sulphur and which is optionally substituted by an alkyl radical.

It is preferred to hydrolyse an enamine of general formula XXIII in which $R^{13}$ and $R^{14}$ each represent a methyl radical.

The reaction is generally carried out in an organic acid (e.g. formic acid or acetic acid) or an inorganic acid (e.g. hydrochloric acid or sulphuric acid), in the presence or absence of a solvent, in an aqueous or organic medium, at a temperature from $-20°$ C. to the reflux temperature of the reaction mixture. If the reaction is carried out in an organic medium, the hydrolysis is carried out by adding water to the reaction mixture and this is followed, if appropriate, by treatment with an inorganic base (alkali metal bicarbonate) or organic base (tertiary amine or pyridine).

If the reaction is carried out in the presence of a solvent, it is not necessary for the solvent to be miscible with the acid aqueous phase. Contact is then achieved by means of brisk stirring.

Chlorinated hydrocarbon solvents, ethyl acetate, tetrahydrofuran, acetonitrile, dimethylformamide and alcohols may be mentioned as solvents which can be used. It is not absolutely necessary, in order to carry out this reaction, to have purified the intermediate of general formula XXIII.

The compounds of general formulae XI, XV or XXII in which n is equal to 1 can be obtained respectively by oxidising the compounds of general formulae XI, XV or XXII in which n is equal to 0, by applying the method described in published German Patent Application No. 2,637,176.

The compounds of general formula XXIII in which $R^{13}$ and $R^{14}$ are as hereinbefore defined, except that they do not represent alkyl substituted by hydroxy, amino or alkylamino, can be obtained by reacting a compound of the general formula:

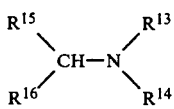         XXIV which is optionally prepared in situ [and wherein $R^{13}$ and $R^{14}$ are as hereinbefore defined and $R^{15}$ and $R^{16}$, which are identical or different, either represent groups of the general formula:

$-X_2R^{17}$         XXV wherein $X_2$ represents an oxygen atom and $R^{17}$ represents an alkyl or phenyl radical, or one of them represents a radical of general formula XXV (wherein $X_2$ represents an oxygen or sulphur atom and $R^{17}$ is alkyl or phenyl) and the other represents an amino radical of the general formula:

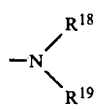         XXVI (wherein $R^{18}$ and $R^{19}$ are as hereinbefore defined for $R^{13}$ and $R^{14}$) or also $R^{15}$ and $R^{16}$ each represent a radical of the general formula XXVII], with a cephalosporin derivative of the general formula:

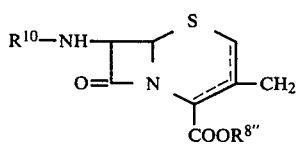         XXVII wherein $R^{8''}$ and $R^{10}$ are as hereinbefore defined and the compound is in the form of a bicyclooct-2-ene or -3-ene or a 3-methylenebicyclooctane.

If a compound of general formula XXIV in which the radical XXVI is different from $-NR^{13}R^{14}$ is chosen, it is preferable to choose this product so that the amine $HNR^{18}R^{19}$ is more volatile than $HNR^{13}R^{14}$.

The reaction is generally carried out in an organic solvent, such as dimethylformamide, or in a mixture of solvents (e.g. dimethylformamide/tetrahydrofuran, dimethylformamide/dimethylacetamide, dimethylformamide/diethyl ether or dimethylformamide/dioxan), at a temperature from 20° C. to the reflux temperature of the reaction mixture.

The compounds of the general formula XXIII in which $R^{8''}$ and $R^{10}$ are as hereinbefore defined and $R^{13}$ and $R^{14}$ represent alkyl radicals substituted by hydroxy, amino or alkylamino can be obtained by trans-enamination from a compound of the general formula XXIII in which $R^{13}$ and $R^{14}$ represent alkyl radicals, preferably methyl.

The reaction is carried out by reacting an amine of the general formula:

         XXVIII (wherein $R^{13'}$ and $R^{14'}$, which are identical or different, represent alkyl radicals substituted by hydroxy, amino, or alkylamino,) with a compound of general formula XXIII, under the conditions described above for the reaction of a compound of general formula XXIV with a compound of the general formula XXVII.

The products of the general formula XXIV can be prepared in accordance with the methods described by H. Bredereck et al., Chem. Ber., 101, 41 (1968), Chem. Ber., 101, 3,058 (1968) and Chem. Ber., 106, 3,725 (1973).

The cephalosporin derivatives of general formula XXVII in which $R^{8''}$ represents a radical of the general formula X can be obtained by esterifying the corresponding acids by any known method for obtaining an ester from an acid without affecting the rest of the molecule.

In general, an alkali metal salt or a tertiary amine salt of a product of the general formula:

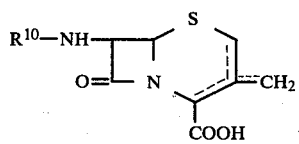         XXIX (wherein $R^{10}$ is as hereinbefore defined) is reacted with a compound of the general formula:

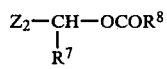         XXX (wherein $R^7$ and $R^8$ are as hereinbefore defined and $Z_2$ represents a halogen atom), in an inert solvent, such as dimethylformamide, at a temperature from 0° to 30° C.

The introduction of the protective groups $R^{8''}$ and $R^{10}$ of the compound of general formula XXVII (or XXIX in the case of $R^{10}$) can be carried out on a 7-aminocephalosporin of the general formula:

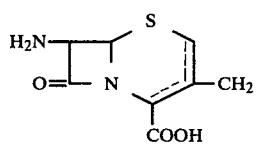         XXXI in which the position of the double bond is defined as above, in accordance with known methods. For example, the methods described in the following literature references:

if $R^{10}$ is a formyl radical: according to J. C. Sheehan et al., J. Amer. Chem. Soc., 80, 1,156 (1958);

if $R^{10}$ is acetyl, chloroacetyl, trichloroacetyl, phenylacetyl, phenoxyacetyl or benzoyl: according to E. H. Flynn, Cephalosporins and Penicillins, Ac. Press (1972);

if $R^{10}$ is a t-butoxycarbonyl radical: according to L. Moroder et al., Hoppe Seyler's Z. Physiol. Chem., 357, 1,651 (1976);

if $R^{10}$ is 2,2,2-trichloro-1,1-dimethylethoxycarbonyl: according to J. Ugi et al., Angew. Chem. Int. Ed. Engl., 17(5), 361 (1978);

if $R^{10}$ is 2,2,2-trichloroethoxycarbonyl, 2-chloro-1,1-dimethylethoxycarbonyl, 2-cyano-1,1-dimethylethoxycarbonyl, 2-trimethylsilylethoxycarbonyl, benzyloxycarbonyl, p-methoxybenzyloxycarbonyl, 3,5-dimethoxybenzyloxycarbonyl, p-nitrobenzyloxycarbonyl or vinyloxycarbonyl: by reaction with a chloroformate in an aqueous-organic medium, in the presence of an alkali metal bicarbonate, or according to Belgian Pat. No. 788,885;

if $R^{10}$ is diphenylmethoxycarbonyl: by reaction with the corresponding azidoformate in an aqueous-organic medium, in the presence of an alkali metal bicarbonate;

if $R^{10}$ is 2-(biphenyl-4-yl)-isopropoxycarbonyl; by analogy with the method described in Helv. Chim. Acta, 51, 924 (1968);

if $R^{10}$ is quinol-8-yl-oxycarbonyl or allyloxycarbonyl: by reaction with the corresponding carbonate in a basic aqueous-organic medium;

if $R^{10}$ is o-nitrophenylthio or p-nitrophenylthio; by analogy with the method described by L. Zervas et al., J. Amer. Chem. Soc., 85, 3,660 (1963);

if $R^{10}NH$ is replaced by dimethylaminomethyleneimino: by analogy with the method described by J. F. Fitt, J. Org. Chem., 42(15), 2,639 (1977);

if $R^{10}NH$ is replaced by 4-nitrobenzylideneimino or 3,4-dimethoxybenzylideneimino: in accordance with the method described by R. A. Sirestone, Tetrahedron Lett., 375 (1972);

if $R^{8''}$ is methoxymethyl: according to S. Seki et al., Tetrahedron Lett., 33, 2,915 (1977);

if $R^{8''}$ is t-butyl: according to R. J. Stedman, J. Med. Chem., 9, 444 (1966);

if $R^{8''}$ is benzhydryl; according to published Dutch Patent Application 73/03,263;

if $R^{8''}$ is p-nitrobenzyl or p-methoxybenzyl: according to R. R. Chauvette et al., J. Org. Chem., 38(17), 2,994 (1973);

The isomers of the compounds of general formulae XI, XV, XXII, XXIII, XXIX and XXXI can be separated by crystallisation or by chromatography.

The cephalosporin derivatives of general formula IX and their pharmaceutically acceptable salts possess particularly valuable antibacterial properties. They exhibit a remarkable in vitro and in vivo activity against Gram-positive and Gram-negative germs.

In vitro, the compound of general formula IX have shown themselves to be active at a concentration of between 0.5 and 15 μg/cc against staphylococcus strains which are sensitive to penicillin G (*Staphylococcus aureus* Smith), at a concentration of between 1 and 30 μg/cc against staphylococcus strains which are resistant to penicillin G (*Staphylococcus aureus* MB 9), at a concentration of between 0.001 and 1 μg/cc against *Escherichia coli*, Monod strain, and at a concentration of between 0.06 and 30 μg/cc against *Klebsiella pneumoniae*. Furthermore, some of these products have shown themselves to be active at a concentration of between 0.01 and 30 μg/cc against *Proteus morganii* and at a concentration of between 0.1 and 30 μg/cc against *Enterobacter aerogenes*.

In vivo, the compounds of the general formula IX have shown themselves to be active at a dose of between 0.2 and 15 mg/kg per day, administered subcutaneously, against experimental infections caused in mice by *Staphylococcus aureus* Smith (sensitive to penicillin G), and at doses of between 0.001 and 10 mg/kg per day, administered subcutaneously, against those infections caused by *Escherichia coli* (Monod strain).

Furthermore, the $LD_{50}$ of the compounds of general formula IX is between 1.5 g/kg and doses of more than 2.5 g/kg, administered subcutaneously to mice.

Of particular value are the compounds of the general formula I in which the symbol R represents:

(1) optionally N-oxidised pyrid-2-yl;

(2) pyrimidin-2-yl or pyridazin-3-yl substituted in the 6-position by a methyl radical and optionally N-oxidised;

(3) 5,6-dioxo-1,4,5,6-tetrahydro-1,2,4-triazin-3-yl substituted in the 4-position by:

(a) an alkyl radical containing 1 to 3 carbon atoms or an alkyl radical containing 1 or 2 carbon atoms and substituted by an alkoxy, alkylthio, phenyl, carbamoyl, dialkylcarbamoyl or alkoxycarbonyl radical, (b) an allyl or 2,3-dihydroxypropyl radical (c) an alkyl radical containing 2 or 3 carbon atoms and substituted by hydroxy, carbamoyloxy, acyloxy (unsubstituted or substituted by amino), amino or acylamino (unsubstituted or substituted by amino), or (d) a radical of the general formula II or III in which alk represents alkylene containing 1 or 2 carbon atoms, $X^\alpha$ and $Y^\alpha$ represent oxygen atoms, $R^\alpha$ represents an alkyl radical and $R^\beta$ represents a hydrogen atom;

(4) 2-alkoxycarbonyl-1,3,4-triazol-5-yl substituted in the 1-position by a radical of general formula II as hereinbefore defined;

(5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl;

(6) 1-alkyl-3-alkoxycarbonyl-1,2,4-triazol-5-yl;

(7) (a) 1,3,4-thiadiazol-5-yl which is unsubstituted or substituted by an alkyl, amino, dialkylaminoalkyl or acylaminoalkyl radical, or (b) 1,2,4-thiadiazol-5-yl substituted by an alkyl radical;

(8) (a) 1,3,4-oxadiazol-5-yl substituted by a phenyl radical, or (b) 4-alkyloxazol-2-yl; or (9) tetrazol-5-yl substituted in the 1-position by:

(a) an alkyl radical, (b) an alkyl radical containing 2 or 3 carbon atoms and substituted by hydroxy, dialkylamino or acylamino, or (c) a radical of general formula II as defined above; the symbol R° represents a hydrogen atom or a methyl, vinyl or cyanomethyl radical and the symbol R' represents a trityl radical, it being understood that the above-mentioned alkyl or acyl moieties or radicals unless otherwise specified contain 1 or 2 carbon atoms, and that the amino or alkylamino groups are protected by a t-butoxycarbonyl radical and the hydroxy groups are protected by a trityl or 2-methoxyprop-2-yl radical, or by a 2,2-dimethyldioxolan-4-yl-methyl radical in the case of the protection of a 2,3-dihydroxypropyl radical.

Particularly preferred compounds of general formula I are those in which R represents:

(1) 5,6-dioxo-1,4,5,6-tetrahydro-1,2,4-triazin-3-yl substituted in the 4-position by:

(a) alkyl containing 2 to 4 carbon atoms and substituted by t-butoxycarbonylamino or acylamino, or (b) a radical of general formula II as hereinbefore defined;

(2) 2-alkyl-1,3,4-thiadiazol-5-yl; or (3) 1-alkyltetrazol-5-yl;

R° is a methyl radical and R' is a trityl radical, the alkyl and acyl moieties and radicals being as just defined above.

The new compounds according to the invention can be purified, if necessary, by physical methods such as crystallisation or chromatography.

The compounds of general formula I in which R contains a carboxy or sulpho radical can also be converted by known methods into metal salts or into addition salts with tertiary nitrogen-containing organic bases. These salts can be obtained by reacting a metal base (e.g. an alkali metal base or alkaline earth metal base) or a tertiary amine with a compound of general formula I, in a suitable solvent, such as an alcohol or an ether, or by means of an exchange reaction with a salt of an organic acid. The salt formed precipitates, after concentration, if necessary, of its solution, and is separated off by filtration or decantation. It can also be isolated from its solution by evaporation of the solvent or by lyophilisation.

Suitable salts include the salts with alkali metals (such as the potassium, sodium or lithium salts) or with alkaline earth metals and the salts of tertiary nitrogen-containing bases (e.g. salts of pyridine, triethylamine, diisopropylethylamine, N-ethylpiperidine and N-methylmorpholine).

These salts can be used, in the same manner as the corresponding acids, for the preparation of cephalosporins of general formula IX.

The following examples illustrate the present invention.

EXAMPLE 1

N,N'-Dicyclohexylcarbodiimide (4.96 g) is added all at once, whilst stirring, to a suspension, cooled to 4° C., of the syn isomer of 2-methoxyimino-2-(2-tritylaminothiazol-4-yl)-acetic acid (8.88 g) and 5-mercapto-2-methyl-1,3,4-thiadiazole (2.64 g) in ethyl acetate (200 cc). The suspension is stirred for 4 hours at 4° C. and filtered, the filtrate is washed with water (2×200 cc), a semi-saturated solution of sodium bicarbonate (2×100 cc) and a saturated solution of sodium chloride (100 cc), dried over sodium sulphate and filtered, the filtrate is concentrated to 20 cc at 20° C. under 20 mm Hg (2.7 kPa) and the residue is filtered. The filtrate is diluted with petroleum ether (200 cc), the mixture is filtered and a yellow powder (6.2 g) corresponding to the expected crude product is collected.

Purification is carried out in the following manner: the above product is treated under reflux with cyclohexane (200 cc), the mixture is filtered hot, the filtrate is concentrated to 30 cc (20° C. under 20 mm Hg; 2.7 kPa), the residue is filtered and the syn isomer of 5-[2-methoxyimino-2-(2-tritylaminothiazol-4-yl)-acetylthio]-2-methyl-1,3,4-thiadiazole (4.5 g) is collected.

Proton NMR spectrum (80 MHz, CDCl$_3$, δ in ppm, J in Hz): 2.85 (s, 3H, —CH$_3$); 4.08 (s, 3H, =NOCH$_3$); 6.60 (s, 1H, H of the thiazole).

Infra-red spectrum (CHBr$_3$), characteristic bands (cm$^{-1}$): 1,695, 1,605, 1,580, 1,530, 1,490, 1,450, 1,050, 900.

EXAMPLE 2

N,N'-Dicyclohexylcarbodiimide (0.50 g) is added all at once to a solution, cooled to 4° C., of the syn isomer of 2-methoxyimino-2-(2-tritylaminothiazol-4-yl)acetic acid (0.89 g) and 4-(2,2-dimethoxyethyl)-5,6-dioxo-3-thioxo-perhydro-1,2,4-triazine (0.47 g) in dimethylformamide (20 cc); the mixture is stirred for 1 hour at 4° C. and then for 3 hours at 20° C. The reaction suspension is filtered, the filtrate is diluted with ethyl acetate (100 cc), the mixture is washed with water (2×50 cc), a 1% strength solution of sodium bicarbonate (2×50 cc) and a semi-saturated solution of sodium chloride (2×50 cc), dried over sodium sulphate and filtered and the filtrate is concentrated to dryness at 20° C. under 20 mm Hg (2.7 kPa). The residue is triturated in isopropyl ether (10 cc) and, after filtration and drying, the syn isomer of 4-(2,2-dimethoxyethyl)-5,6-dioxo-3-[2-methoxyimino-2-(2-tritylaminothiazol-4-yl)-acetylthio]-1,4,5,6-tetrahydro-1,2,4-triazine (0.91 g) is obtained in the form of a yellow powder.

Proton NMR spectrum (80 MHz, CDCl$_3$, δ in ppm, J in Hz): 3.30 (s, 6H, —OCH$_3$); 4.05 (s, 3H, =NOCH$_3$); 4.28 (d, J=5, 2H, >NCH$_2$—); 4.66 (t, J=5, 1H, —CH=); 6.68 (s, 1H, H of the thiazole).

Infra-red spectrum (CHBr$_3$), characteristic bands (cm$^{-1}$): 3,380, 1,720, 1,585, 1,525, 1,490, 1,450, 1,040, 900, 750, 730.

4-(2,2-Dimethoxyethyl)-5,6-dioxo-3-thioxo-perhydro-1,2,4-triazine can be prepared in the following manner:

A solution of sodium methylate is prepared by dissolving sodium (4.15 g) in methanol (140 cc), 4-(2,2-dimethoxyethyl)-thiosemicarbazide (32.3 g) is added and ethyl oxalate (26.3 g) is added. The mixture is heated under reflux for 4 hours, whilst stirring, and left to cool. After one night, the suspension obtained is filtered and the precipitate is washed with ether (3×25 cc). The solid is dissolved in water (40 cc) and, after cooling to about 4° C., the solution is acidified to pH 3 with 4 N hydrochloric acid and left at 4° C. for 30 minutes. After filtration and drying, 4-(2,2-dimethoxyethyl)-5,6-dioxo-3-thioxo-perhydro-1,2,4-triazine (12 g) is collected in the form of a white solid. Inst. m.p. (Kolfer)=172° C. (decomposition).

Infra-red spectrum (KBr), characteristic bands (cm$^{-1}$): 3,280, 3,250, 1,695, 1,380, 1,130, 1050.

Proton NMR spectrum (80 MHz, DMSO-d$_6$, δ in ppm, J in Hz): 3.30 (s, 6H, —OCH$_3$); 4.38 (d, J=5.5, 2H, >NCH$_2$—); 4.94 (t, J=5.5, 1H, —CH(OCH$_3$)$_2$).

4-(2,2-Dimethoxyethyl)-thiosemicarbazide can be prepared in the following manner:

2,2-Dimethoxyethyl isothiocyanate (37.7 g) is added in the course of 1 hour, at a temperature between 5° and 9° C., whilst stirring, to a solution of hydrazine hydrate (14.35 g) in ethanol (40 cc). After 12 hours at 4° C., the mixture is concentrated to dryness at 20° C. under reduced pressure (20 mm Hg; 2.7 kPa). The yellow syrup obtained crystallises after seeding. The solid is dissolved in hot methanol (50 cc), the solution is filtered and the filtrate is diluted with diethyl ether (200 cc). After about ten hours at 4° C., the mixture is filtered and 4-(2,2-dimethoxyethyl)-thiosemicarbazide (32.3 g) is collected in the form of a white solid. Inst. m.p. (Kofler)=69° C.

EXAMPLE 3

N,N'-Dicyclohexylcarbodiimide (1.11 g) is added to a suspension, cooled to +4° C., of the syn isomer of 2- methoxyimino-2-(2-tritylaminothiazol-4-yl)-acetic acid (2.17 g) and 4-(2-t-butoxycarbonylaminoethyl)-5,6-dioxo-3-thioxo-perhydro-1,2,4-triazine (1.05 g) in ethyl acetate (50 cc). The mixture is stirred for 4 hours at 20° C. and filtered and the filtrate is concentrated to dryness at 20° C. under 20 mm Hg (2.7 kPa).

The residue is taken up in methylene chloride (20 cc) and the solution is poured into diisopropyl ether (250 cc). After filtration and drying, the syn isomer of 4-(2-t-butoxycarbonylaminoethyl)-5,6-dioxo-3-[2-methoxyimino-2-(2-tritylaminothiazol-4-yl)acetylthio]-1,4,5,6-tetrahydro-1,2,4-triazine (0.73 g) is collected in the form of a yellow powder.

Infra-red spectrum (CHBr$_3$), characteristic bands (cm$^{-1}$): 3,440, 3,390, 2,820, 1,710, 1,585, 1,530, 1,450, 1,390, 1,370, 1,050, 955, 900, 755.

4-(2-t-Butoxycarbonylaminoethyl)-5,6-dioxo-3-thioxo-perhydro-1,2,4-triazine can be prepared in the following manner:

4-(2-t-butoxycarbonylaminoethyl)-thiosemicarbazide (9.37 g) is added, at 20° C., to a solution of sodium (0.92 g) in methanol (40 cc), and diethyl oxalate (5.4 g) is added dropwise in the course of 10 minutes. The mixture is heated under reflux for 3 hours. It is left to cool, water (100 cc) is added, concentrated hydrochloric acid (3 cc) is added dropwise, the mixture is extracted with ethyl acetate (2×100 cc), the extract is washed with a saturated solution of sodium chloride (2×50 cc), dried over sodium sulphate and filtered and the filtrate is concentrated to dryness at 20° C. under 20 mm Hg (2.7 kPa). The residue is taken up in methylene chloride (65 cc), crystallisation is seeded, the mixture is left for 2 hours at 20° C. and filtered and white crystals of 4-(2-t-butoxycarbonylaminoethyl)-5,6-dioxo-3-thioxo-perhydro-1,2,4-triazine (4.59 g), melting at 160° C., are collected.

Infra-red spectrum (KBr), characteristic bands (cm$^{-1}$): 3,380, 3,150, 1,685, 1,640, 1,545, 1,370.

Proton NMR spectrum (80 MHz, DMSO-d$_6$, δ in ppm, J in Hz): 1.45 (s, 9H, —C(C$\underline{H}_3$)$_3$); 3.32 (q, J=5, 2H, —CH$_2$C$\underline{H}_2$NH—); 4.38 (t, J=5, 2H, —C$\underline{H}_2$—CH$_2$—NH—); 6.72 (d, J=5, 1H, CH$_2$CH$_2$N$\underline{H}$—); 12.3 (s broad, 1H, —NH— triazine).

4-(2-t-Butoxycarbonylaminoethyl)-thiosemicarbazide can be prepared in the following manner:

A mixture of methyl N-(2-t-butoxycarbonylaminoethyl)-dithiocarbamate (22.53 g), ethanol (90 cc) and hydrazine hydrate (4.4 cc) is heated under reflux for 1 hour 30 minutes. The solution is concentrated to dryness at 30° C. under 20 mm Hg (2.7 kPa) and the residue is triturated in the presence of diethyl ether (100 cc). Crystallisation starts in the course of 5 minutes. The mixture is left for 1 hour at 20° C. and filtered and the solid is dried. This yields pinkish-white crystals of 4-(2-t-butoxycarbonylaminoethyl)-thiosemicarbazide (11.3 g), melting at 85° C.

Infra-red spectrum (CHBr$_3$), characteristic bands (cm$^{-1}$): 3,450, 3,350, 1,700, 1,620, 1,545, 1,510, 1,390, 1,370, 1,250, 1,225 and 1,160.

Proton NMR spectrum (80 MHz, CDCl$_3$, δ in ppm, J in Hz): 1.48 (s, 9H, —C(CH$_3$)$_3$); 3.45 and 3.80 (2t, J=5, 4H, —CH$_2$CH$_2$—).

Triethylamine (15.5 cc) is added to a solution of 2-t-butoxycarbonylaminoethylamine (17.62 g) in 95% strength ethanol (110 cc), and carbon disulphide (6.65 cc) is added dropwise in the course of 10 minutes, whilst keeping the temperature between 20° C. and 25° C. The mixture is stirred for 1 hour 30 minutes at 22° C. Methyl iodide (6.85 cc) is then added and the mixture is stirred for 1 hour 30 minutes at 22° C. It is concentrated to dryness at 20° C. under 20 mm Hg (2.7 kPa), the residue is taken up in ethyl acetate (200 cc), the mixture is washed with water (3×100 cc), dried over sodium sulphate and filtered and the filtrate is concentrated to dryness at 20° C. under 20 mm Hg (2.7 kPa). Methyl N-(2-t-butoxycarbonylaminoethyl)-dithiocarbamate (23.2 g) is collected in the form of a yellow oil.

Infra-red spectrum (CHBr$_3$), characteristic bands (cm$^{-1}$): 3,440, 3,370, 1,700, 1,505, 1,430, 1,380, 1,370. 945.

Proton NMR spectrum (60 MHz, CDCl$_3$, δ in ppm, J in Hz): 1.50 (s, 9H, —C(CH$_3$)$_3$); 2.65 (s, 3H, —CH$_3$); 3.50 and 3.80 (2t, J=5, 4H, —CH$_2$—CH$_2$—).

2-t-Butoxycarbonylaminoethylamine is prepared by hydrazinolysis of N-t-butoxycarbonyl-phthalimidoethylamine:

Hydrazine hydrate (10.8 cc) is added to a suspension of N-t-butoxycarbonyl-2-phthalimidoethylamine (53.7 g) in ethanol (540 cc) and the mixture is heated under reflux for 25 minutes. The mixture is cooled to 0° C. and filtered. The filtrate is concentrated to dryness under reduced pressure (20 mm Hg; 2.7 kPa). This yields 2-(N-t-butoxycarbonylamino)-ethylamine (19.6 g) in the form of a yellow oil.

Infra-red spectrum (CHCl$_3$), characteristic bands (cm$^{-1}$): 3,460, 3,380, 3,320, 1,700, 1,585, 1,500, 1,390, 1,370, 1,160, 490.

Proton NMR spectrum (60 MHz, CDCl$_3$, δ in ppm, J in Hz): 1.48 (s, 9H, —C(C$\underline{H}_3$)$_3$); 2.20 (s broad, 2H, —NH$_2$); 2.80 (t, J=5, 2H, H$_2$N—C$\underline{H}_2$—CH$_2$—); 3.18 (t, J=5, 2H, H$_2$NCH$_2$C$\underline{H}_2$—); 5.50 (s broad, 1H, —NHCO—).

EXAMPLE 4

5-Mercapto-1-methyltetrazole (1.16 g) and N,N'-dicyclohexylcarbodiimide (2.47 g) are added successively to a solution, cooled to +5° C., of the syn isomer of 2-methoxyimino-2-(2-tritylaminothiazol-4-yl)-acetic acid (4.43 g) in ethyl acetate (100 cc). The mixture is stirred for 3 hours 30 minutes at 20° C. and filtered, the filtrate is washed with a saturated solution of sodium bicarbonate (100 cc), water (100 cc) and water saturated with sodium chloride (100 cc), dried over sodium sulphate and filtered and the filtrate is concentrated to dryness at 20° C. under 20 mm Hg (2.7 kPa). The residue is stirred for 2 hours in isopropyl ether (50 cc), the mixture is filtered and, after drying, the syn isomer of 5-[2-methoxyimino-2-(2-tritylaminothiazol-4-yl)acetylthio]-1-methyltetrazole (4.67 g) is collected in the form of a yellow powder.

Infra-red spectrum (CHBr$_3$), characteristic bands (cm$^{-1}$): 3,395, 1,720, 1,530, 1,490, 1,450, 1,050, 900, 750, 730.

EXAMPLE 5

4-(2-Acetamidoethyl)-5,6-dioxo-3-thioxo-perhydro-1,2,4-triazine (2.30 g) and N,N'-dicyclohexylcarbodiimide (2.48 g) are added successively to a solution, cooled to +5° C., of the syn isomer of 2-methoxyimino-2-(2-tritylaminothiazol-4-yl)-acetic acid (4.44 g) in dimethylformamide (100 cc). The mixture is stirred for 3 hours at 20° C., acetic acid (0.5 cc) is added and the mixture is stirred for a further 15 minutes and filtered. The filtrate is diluted with ethyl acetate (480 cc), the mixture is washed with water (2×240 cc) and water saturated with sodium chloride (240 cc), dried over sodium sulphate and filtered and the filtrate is concentrated to dryness at 20° C. under 20 mm Hg (2.7 kPa). The syn isomer of 4-(2-acetamidoethyl)-5,6-dioxo-3-[2-methoxyimino-2-(2-tritylaminothiazol-4-yl)-acetylthio]-1,4,5,6-tetrahydro-1,2,4-triazine (6.5 g) is collected in the form of a crude, hard cream-coloured foam.

Rf=0.125 [silica gel chromatography plate, eluant: ethyl acetate/methanol (95/5 by volume)].

Infra-red spectrum (CHBr$_3$), characteristic bands (cm$^{-1}$): 3,380, 1,725, 1,705, 1,675, 1,525, 1,450, 1,370, 1,245, 1,040, 750.

4-(2-Acetamidoethyl)-5,6-dioxo-3-thioxo-perhydro-1,2,4-triazine (3.61 g) {inst. m.p. [Kofler]>260° C.; infra-red spectrum (KBr), characteristic bands (cm$^{-1}$): 3,365, 3,050, 2,000, 1,710, 1,630, 1,600–1,580, 1,545, 1,350, 1,330, 1,200; proton NMR spectrum (80 MHz, DMSO-d$_6$, δ in ppm, J in Hz): 1.7 (s, 3H, —CH$_3$); 3 to 3.7 (mt, —CH$_2$NHCO— and H$_2$O); 4.3 (t, 2H, >NCH$_2$—); 7.85 (t, 1H, —NHCO—); 12.5 (m, 2H, —NH— of the ring)} is prepared from 4-(2-acetamido-ethyl)-thiosemicarbazide (4.41 g) and ethyl oxalate (3.4 cc), in the presence of sodium methylate, by applying the method described by M. Pesson and M. Antoine, Bull. Soc. Chim. France, 1,590 (1970).

The starting thiosemicarbazide can be obtained in accordance with the following procedure:

A solution of methyl N-(2-acetamidoethyl)-dithiocarbamate (57.7 g) and hydrazine hydrate (14.6 cc) in absolute ethanol (300 cc) is heated under reflux for 2 hours. The mixture is cooled to 4° C. and filtered and the insoluble material is dried at 30° C. under 0.05 mm Hg. This yields 4-(2-acetamidoethyl)-thiosemicarbazide (39.5 g) in the form of white crystals (inst. m.p. [Kofler]=171° C.).

Infra-red spectrum (KBr), characteristic bands (cm$^{-1}$): 3,280, 3,180, 1,650, 1,560 to 1,535, 1,360, 1,280.

The products according to the invention can be used for the preparation of the products of the general formula (IX) in accordance with the following procedures:

REFERENCE EXAMPLE A

The product of Example 1 can be used in the following manner:

A mixture of the E form of 7-amino-2-benzhydryloxycarbonyl-8-oxo-3-(2-tosyloxyvinyl)-5-thia-1-azabicyclo[4.2.0]oct-2-ene-5-oxide (1.16 g), dimethylformamide (35 cc), the syn isomer of 5-[2-methoxyimino-2-(2-tritylaminothiazol-4-yl)-acetylthio]-2-methyl-1,3,4-thiadiazole (1.67 g) and N,N-diisopropylethylamine (0.35 cc) is stirred for 1 hour at 60° C. and under nitrogen. The mixture is diluted with ethyl acetate (140 cc), the solution is washed with water (3×70 cc), dried over sodium sulphate and filtered and the filtrate is concentrated to dryness at 20° C. under 20 mm Hg (2.7 kPa). The residue is taken up in methylene chloride (25 cc), Merck silica gel (0.06–0.2 mm) (5 g) is added, the mixture is concentrated to dryness at 20° C. under 20 mm Hg (2.7 kPa) and the powder is deposited on a column of Merck silica gel (0.06–0.2) (35 g) (diameter of the column: 2 cm). Elution is carried out successively with an 80/20 (by volume) mixture of cyclohexane and ethyl acetate (100 cc), a 60/40 (by volume) mixture (250 cc), a 40/60 (by volume) mixture (500 cc), a 20/80 (by volume) mixture (500 cc) and pure ethyl acetate (500 cc), 60 cc fractions being collected. Fractions 17 to 26 are concentrated to dryness at 20° C. under 20 mm Hg (2.7 kPa) and the E form of the syn isomer of 2-benzhydryloxycarbonyl-7-[2-methoxyimino-2-(2-tritylaminothiazol-4-yl)-acetamido]-3-[2-(2-methyl-1,3,4-thiadiazol-5-yl-thio)-vinyl]-8-oxo-5-thia-1-azabicyclo[4.2.0]oct-2-ene-5-oxide (0.56 g) is collected in the form of a hard pink foam.

Infra-red spectrum (CHBr$_3$), characteristic bands (cm$^{-1}$): 3,380, 1,800, 1,725, 1,680, 1,515, 1,490, 1,445, 1,045, 935, 750.

Proton NMR spectrum (350 MHz, CDCl$_3$, δ in ppm, J in Hz): 2.72 (s, 3H, —CH$_3$); 3.28 and 4.08 (2d, J=18, 2H, —SCH$_2$—); 4.07 (s, 3H, —OCH$_3$); 4.60 (d, J=4, 1H, H in the 6-position); 6.16 (dd, J=4 and 9, 1H, H in the 7-position); 6.71 (s, 1H, H of the thiazole);

6.95 (s, 1H, —COOCH—);
                    |

7.07 (s, 1H, —NHC(C$_6$H$_5$)$_3$); 7.23 and 7.33 (2d, J=16, —CH=CH—).

Phosphorus trichloride (0.93 cc) is added, at −8° C. and whilst stirring, to a solution of the E form of the syn isomer of 2-benzhydryloxycarbonyl-7-[2-methoxyimino-2-(2-tritylaminothiazol-4-yl)-acetamido]-3-[2-(2-methyl-1,3,4-thiadiazol-5-yl)-thiovinyl]-8-oxo-5-thia-1-azabicyclo[4.2.0]oct-2-ene-5-oxide (5.11 g) and dimethylacetamide (2.1 cc) in methylene chloride (50 cc). The mixture is stirred for 1 hour at −8° C. and diluted with ethyl acetate (1 liter) and the resulting mixture is washed with a semi-saturated solution of sodium bicarbonate (2×250 cc) and a semi-saturated solution of sodium chloride (2×250 cc), dried over sodium sulphate and concentrated to dryness at 20° C. under 20 mm Hg (2.7 kPa). The product, dissolved in a 40/60 (by volume) mixture of cyclohexane and ethyl acetate (50 cc), is chromatographed on a column of Merck silica gel (0.04–0.06) (150 g) (diameter of the column: 5 cm). Elution is carried out with the above mixture (3 liters) under a pressure of 4 kPa, 125 cc fractions being collected. Fractions 10 to 20 are concentrated to dryness at 20° C. under 20 mm Hg (2.7 kPa). The E form of the syn isomer of 2-benzhydryloxycarbonyl-7-[2-methoxyimino-2-(2-tritylaminothiazol-4-yl)-acetamido]-3-[2-(2-methyl-1,3,4-thiadiazol-5-yl)-thiovinyl]-8-oxo-5-thia-1-azabicyclo[4.2.0]oct-2-ene (2.69 g) is collected in the form of a hard yellow foam.

Infra-red spectrum (CHBr$_3$), characteristic bands (cm$^{-1}$): 3,390, 1,785, 1,720, 1,685, 1,515, 1,495, 1,445, 1,045, 940, 755.

Proton NMR spectrum (350 MHz, CDCl$_3$, δ in ppm, J in Hz): 2.75 (s, 3H, —CH$_3$); 3.60 and 3.69 (2d, J=18, 2H, —SCH$_2$—); 4.09 (s, 3H, —OCH$_3$); 5.09 (d, J=4, 1H, H in the 6-position); 5.93 (dd, J=4 and 9, 1H, H in the 7-position); 6.75 (s, 1H, H of the thiazole);

6.98 (s, 1H, —COOCH—);
                    |

7.0 (s, 1H, —NHC(C$_6$H$_5$)$_3$); 7.22 (d, J=14, 1H, —CH=CHS—).

A mixture of the E form of the syn isomer of 2-benzhydryloxycarbonyl-7-[2-methoxyimino-2-(2-tritylaminothiazol-4-yl)-acetamido]-3-[2-(2-methyl-1,3,4-thiadiazol-5-yl)-thiovinyl]-8-oxo-5-thia-1-azabicyclo[4.2.0]oct-2-ene (2.37 g) in formic acid (30 cc) to which water (14 cc) has been added is stirred at 50° C. for 15 minutes. It is left to cool and diluted with water (16 cc) and the mixture is filtered. The filtrate is concentrated to dryness at 30° C. under 0.05 mm Hg (0.007 kPa) and the residue is taken up in ethanol (3×50 cc), the mixture being concentrated to dryness each time. The solid obtained is stirred at 50° C. in ethanol (35 cc) for 25 minutes, filtered off, washed with ethyl ether (2×20 cc) and dried. The E form of the syn isomer of 7-[2-(2-aminothiazol-4-yl)-2-methoxyiminoacetamido]-2-carboxy-3-[2-(2-methyl-1,3,4-thiadiazol-5-yl)-thiovinyl]-8-oxo-5-thia-1-azabicyclo[4.2.0]oct-2-ene (1.18 g) is collected in the form of a yellow powder.

Infra-red spectrum (KBr), characteristic bands (cm$^{-1}$): 3,400, 3,200, 3,100, 2,200, 1,775, 1,675, 1,530, 1,045, 940.

Proton NMR spectrum (350 MHz, DMSO-d$_6$, δ in ppm, J in Hz): 2.74 (s, 3H, —CH$_3$); 3.67 and 3.94 (2d, J=18, 2H, —SCH$_2$—); 3.86 (s, 3H, —OCH$_3$); 5.21 (d, J=4, 1H, H in the 6-position); 5.80 (2d, J=4 and 9, 1H, H in the 7-position); 6.75 (s, 1H, H of the thiazole); 7.12 and 7.17 (2d, J=16, 2H, —CH=CHS—); 7.20 (s, 2H, —NH$_2$); 9.63 (d, J=9, 1H, —CONH—).

The E form of 7-amino-2-benzhydryloxycarbonyl-8-oxo-3-(2-tosyloxyvinyl)-5-thia-1-azabicyclo[4.2.0]oct-2-ene-5-oxide can be obtained in the following manner:

A solution of the E form of 2-benzhydryloxycarbonyl-7-t-butoxycarbonylamino-8-oxo-3-(2-tosyloxyvinyl)-5-thia-1-azabicyclo[4.2.0]oct-2-ene-5-oxide (54.3 g) and hydrated p-toluenesulphonic acid (30.4 g) in acetonitrile (1.4 liters) is stirred at 35° C. for 2 hours. The mixture is concentrated to dryness at 30° C. under 20 mm Hg (2.7 kPa), the residue is taken up in ethyl acetate (1 liter) and the mixture is washed with a semi-saturated solution of sodium bicarbonate (2×500 cc) and a semi-saturated solution of sodium chloride (2×500 cc), dried over sodium sulphate and concentrated to dryness at 20° C. under 20 mm Hg (2.7 kPa). The residue is triturated in ether (200 cc). This yields the E form of 7-amino-2-benzhydryloxycarbonyl-8-oxo-3-(2-tosyloxyvinyl)-5-thia-1-azabicyclo[4.2.0]oct-2-ene-5-oxide (28.13 g) in the form of a light brown powder. Rf=0.32; silica gel chromatography plate [methylene chloride/methanol 85/15 (by volume)].

2-Benzhydryloxycarbonyl-7-t-butoxycarbonylamino-8-oxo-3-(2-tosyloxyvinyl)-5-thia-1-azabicyclo[4.2.0]oct-2-ene-5-oxide can be prepared in the following manner:

A solution of 85% pure m-chloroperbenzoic acid (55.22 g) in methylene chloride (600 cc) is added dropwise, in the course of 2 hours, to a solution, cooled to −10° C., of 2-benzhydryloxycarbonyl-7-t-butoxycarbonylamino-8-oxo-3-(2-tosyloxyvinyl)-5-thia-1-azabicyclo[4.2.0]oct-2-ene (or -3-ene) (mixture of the E and Z forms) (180.56 g) in methylene chloride (1.4 liters). The mixture is washed with a 5% strength solution of sodium bicarbonate (1.5 liters) and water (2×1.5 liters), dried over sodium sulphate and concentrated at 20° C. under reduced pressure (20 mm Hg; 2.7 kPa) to a volume of 300 cc. This solution is chromatographed on a column of Merck silica gel (0.05-0.2) (3 kg) (diameter of the column: 9.2 cm; height: 145 cm). Elution is carried out successively with the following mixtures of cyclohexane and ethyl acetate: 80/20 (by volume) (15 liters) and 70/30 (by volume) (32 liters), 600 cc fractions being collected. Fractions 27 and 28 are collected and evaporated and this yields the Z form of 2-benzhydryloxycarbonyl-7-t-butoxycarbonylamino-8-oxo-3-(2-tosyloxyvinyl)-5-thia-1-azabicyclo[4.2.0]oct-2-ene-5-oxide (5.56 g).

Infra-red spectrum (CHBr$_3$), characteristic bands (cm$^{-1}$): 3,420, 1,800, 1,720, 1,505, 1,380, 1,370, 1,195, 1,180, 1,050, 1,010, 730.

Proton NMR spectrum (350 MHz, CDCl$_3$, δ in ppm, J in Hz): 1.49 (s, 9H, —C(CH$_3$)$_3$); 2.44 (s, 3H, —CH$_3$); 3.36 and 4.04 (2d, J=19, 2H, —SCH$_2$—); 4.44 (d, J=4.5, 1H, H in the 6-position); 5.73 (d, J=9, 1H, —CONH—); 5.81 (dd, J=4.5 and 9, 1H, H in the 7-position); 6.42 (d, J=7, 1H, —CH=CH—OSO$_2$—); 6.46 (d, J=7, 1H, =CH—OSO$_2$—); 6.89 (s, 1H, —COOCH<); 7.77 (d, J=9, 2H, H in the ortho-position of the tosyl).

A mixture of the Z and E forms (26 g) is obtained from fractions 29 to 34.

Finally, the E form of the product (43 g) is obtained from fractions 35 to 58:

Infra-red spectrum (CHBr$_3$), characteristic bands (cm$^{-1}$): 3,420, 1,800, 1,720, 1,505, 1,380, 1,370, 1,195, 1,180, 1,075, 935, 745.

Proton NMR spectrum (350 MHz, CDCl$_3$, δ in ppm, J in Hz): 1.48 (s, 9H, (CH$_3$)$_3$C—); 2.46 (s, 3H, —CH$_3$); 3.16 and 3.81 (2d, J=18, 2H, —SCH$_2$—); 4.46 (d, J=4.5, 1H, H in the 6-position); 5.73 (d, J=9, 1H, —CONH—); 5.8 (dd, J=9 and 4.5, 1H, H in the 7-position); 6.83 (d, J=13, 1H, —CH=CH—OSO$_2$—); 6.83 (s, 1H, —COOCH<); 7.08 (d, J=13, 1H, =CH—OSO$_2$—); 7.73 (d, J=9, 2H, H in the ortho-position of the tosyl).

2-Benzhydryloxycarbonyl-7-t-butoxycarbonylamino-8-oxo-3-(2-tosyloxyvinyl)-5-thia-1-azabicyclo[4.2.0]oct-2-ene (or -3-ene) (mixture of the E and Z forms) can be obtained in the following manner:

A solution of formic acid (50 cc) in water (500 cc) is added to a solution of 2-benzhydryloxycarbonyl-7-t-butoxycarbonylamino-3-(2-dimethylaminovinyl)-8-oxo-5-thia-1-azabicyclo[4.2.0]oct-2-ene (E form) (113.7 g) in tetrahydrofuran (1 liter). The homogeneous solution is stirred at 20° C. for 20 minutes and is then concentrated to one quarter of its volume under reduced pressure (20 mm Hg; 2.7 kPa, at 20° C.). The concentrate is taken up in ethyl acetate (2 liters), the mixture is washed with a 5% strength solution of sodium bicarbonate (2×500 cc), water (2×500 cc) and a saturated solution of sodium chloride (2×500 cc), dried over sodium sulphate and filtered and the filtrate is evaporated to dryness at 20° C. under reduced pressure (20 mm Hg; 2.7 kPa). A crude product (112.4 g) is collected and this is treated, in solution in pyridine (250 cc) at 5° C., with tosyl chloride (57.2 g). After 30 minutes at 5° C. and 1 hour at 20° C., the solution is poured into a mixture of water and crushed ice (1 liter). The aqueous phase is separated off and the insoluble material is washed with distilled water (300 cc). The pasty product is dissolved in ethyl acetate (200 cc) and the solution is washed with 1 N hydrochloric acid (2×750 cc), a 5% strength solution of sodium bicarbonate (2×750 cc) and water (4×750 cc), dried over sodium sulphate and concentrated to dryness under reduced pressure (20 mm Hg; 2.7 kPa, at 20° C.). This yields 2-benzhydryloxycarbonyl-7-t-butoxycarbonylamino-8-oxo-3-(2-tosyloxyvinyl)-5-thia-1-azabicyclo[4.2.0]oct-2-ene (or -3-ene) (mixture of the E and Z forms) (121 g) in the form of a crude, hard brown foam.

A mixture of E and Z forms of 2-benzhydryloxycarbonyl-7-t-butoxycarbonylamino-3-(2-dimethylaminovinyl)-8-oxo-5-thia-1-azabicyclo[4.2.0]oct-2-ene and -3-ene can be obtained in accordance with the following procedure:

2-Benzhydryloxycarbonyl-7-t-butoxycarbonylamino-3-methyl-8-oxo-5-thia-1-azabicyclo[4.2.0]oct-2-ene (90.5 g) is dissolved in anhydrous N,N-dimethylformamide (400 cc). The solution obtained is heated to 80° C. under a nitrogen atmosphere. A solution of bis-dimethylamino-t-butoxymethane (36.1 g) in anhydrous N,N-dimethylformamide (60 cc), preheated to 80° C., is then added rapidly. The reaction mixture is kept at 80° C. for 5 minutes and then poured into ethyl acetate (3 liters). After the addition of distilled water (1 liter), the organic phase is decanted, washed with distilled water (4×1 liter), dried over sodium sulphate and filtered in the presence of decolorising charcoal. The filtrate is concentrated to dryness under reduced pressure (20 mm Hg; 2.7 kPa) at 30° C. and this yields 2-benzhydryloxycarbonyl-7-t-butoxycarbonylamino-3-(2-dimethylaminovinyl)-8-oxo-5-thia-1-azabicyclo[4.2.0]oct-2-ene (E form) (101 g) in the form of a hard orange form.

Rf=0.29; silica gel chromatography plate [cyclohexane/ethyl acetate 50/50 (by volume)].

2-Benzhydryloxycarbonyl-7-t-butoxycarbonylamino-3-methyl-8-oxo-5-thia-1-azabicyclo[4.2.0]oct-2-ene can be obtained in the following manner:

A solution of diphenyldiazomethane (116.5 g) in acetonitrile (800 cc) is added dropwise, in the course of 45 minutes, at a temperature between 25° and 30° C., to a solution of 7-t-butoxycarbonylamino-2-carboxy-3-methyl-8-oxo-5-thia-1-azabicyclo[4.2.0]oct-2-ene (188.6 g) in acetonitrile (2,100 cc). The reaction mixture is stirred for 16 hours at 22° C. and then concentrated to dryness under reduced pressure (20 mm Hg; 2.7 kPa) at 40° C. The residue is redissolved in ethyl acetate (2 liters) and the solution is washed with 2 N hydrochloric acid (700 cc) and then with a saturated aqueous solution of sodium bicarbonate (700 cc) and a saturated aqueous solution of sodium chloride (700 cc). The solution is dried over sodium sulphate, treated with decolorising charcoal and filtered and the filtrate is then concentrated to dryness under reduced pressure (20 mm Hg; 2.7 kPa) at 40° C. The residue is dissolved in boiling ethyl acetate (600 cc). Cyclohexane (1 liter) is added and the mixture is heated to the reflux temperature and then left to cool. The crystals which have appeared are filtered off, washed with diethyl ether (3×250 cc) and then dried. This yields 2-benzhydryloxycarbonyl-7-t-butoxycarbonylamino-3-methyl-8-oxo-5-thia-1-azabicyclo[4.2.0]oct-2-ene (191 g) in the form of white crystals (m.p.=179° C.). By concentrating the mother liquors to 500 cc, a second fraction of product (32.6 g, m.p.=178° C.) is obtained.

7-t-Butoxycarbonylamino-2-carboxy-3-methyl-8-oxo-5-thia-1-azabicyclo[4.2.0]oct-2-ene can be obtained in the following manner:

7-Amino-2-carboxy-3-methyl-8-oxo-5-thia-1-azabicyclo[4.2.0]oct-2-ene (371 g) is dissolved in a solution of sodium bicarbonate (307 g) in a mixture of distilled water (2 liters) and dioxane (2 liters). A solution of di-t-butyl dicarbonate (421 g) in dioxane (2 liters) is added in the course of 10 minutes. The reaction mixture is stirred for 48 hours at 25° C. The suspension obtained is concentrated under reduced pressure (20 mm Hg; 2.7 kPa) at 50° C. to a residual volume of about 2 liters and is then diluted with ethyl acetate (1 liter) and distilled water (2 liters). The aqueous phase is separated off by decantation, washed with ethyl acetate (500 cc) and acidified to pH=2 with 6 N hydrochloric acid, in the presence of ethyl acetate (1,500 cc). The aqueous phase is extracted with ethyl acetate (2×1 liter). The combined organic phases are washed with a saturated solution of sodium chloride (2×250 cc) and dried over sodium sulphate. After filtration, the solvent is evaporated off under reduced pressure (20 mm Hg; 2.7 kPa) at 50° C. This yields 7-t-butoxycarbonylamino-2-carboxy-3-methyl-8-oxo-5-thia-1-azabicyclo[4.2.0]oct-2-ene (486 g) in the form of yellow crystals (m.p.=190° C., decomposition).

REFERENCE EXAMPLE B

The product of Example 2 can be used in the following manner:

A mixture of the E form of 7-amino-2-benzhydryloxycarbonyl-8-oxo-3-(2-tosyloxyvinyl)-5-thia-1-azabicyclo[4.2.0]oct-2-ene-5-oxide (0.23 g), dimethylformamide (15 cc), the syn isomer of 4-(2,2-dimethoxyethyl)-5,6-dioxo-3-[2-methoxyimino-2-(2-tritylaminothiazol-4-yl)-acetylthio]-1,4,5,6-tetrahydro-1,2,4-triazine (0.40 g) and N,N-diisopropylethylamine (0.07 cc) is stirred for 5 hours, at 60° C. and under nitrogen. It is diluted with ethyl acetate (60 cc), the solution is washed with water (3×30 cc) and then with a semi-saturated solution of sodium chloride (2×30 cc), dried over sodium sulphate and filtered and the filtrate is concentrated to dryness at 20° C. under 20 mm Hg (2.7 kPa). The residue is taken up in methylene chloride (10 cc), Merck silica gel (0.06–0.2) (2 g) is added and the mixture is concentrated to dryness at 20° C. under 20 mm Hg (2.7 kPa). The powder obtained is deposited on a column of Merck silica gel (0.06–0.2) (8 g) (diameter of the column: 1.2 cm). Elution is carried out successively with an 80/20 (by volume) mixture of cyclohexane and ethyl acetate (50 cc), a 60/40 (by volume) mixture (100 cc), a 40/60 (by volume) mixture (100 cc), a 20/80 (by volume) mixture (200 cc) and pure ethyl acetate (200 cc), 25 cc fractions being collected. Fractions 12 to 19 are concentrated to dryness at 20° C. under 20 mm Hg (2.7 kPa) and the E form of the syn isomer of 2-benzhydryloxycarbonyl-3-{2-[4-(2,2-dimethoxyethyl)-5,6-dioxo-1,4,5,6--tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (0.19 g) is collected in the form of a hard beige foam.

Infra-red spectrum (KBr), characteristic bands (cm$^{-1}$): 3,380, 3,250, 1,795, 1,720, 1,685, 1,520, 1,490, 1,445, 1,040, 940, 760, 700.

Proton NMR spectrum (350 MHz, CDCl$_3$, δ in ppm, J in Hz): 3.34 and 4.12 (2d, J=18, 2H, —SCH$_2$—); 3.40 (s, 6H, —OCH$_3$); 3.94 to 4.06 (m, 5H, —OCH$_3$ and >NCH$_2$—); 4.60 to 4.68 (m, 2H, H in the 6-position and —CH(OCH$_3$)$_2$); 6.07 (dd, J=4 and 9, 1H, H in the 7-position); 6.70 (s, 1H, H of the thiazole); 6.82 (d, J=16, 1H, —CH=CHS—); 6.96 (s, 1H, —COOCH—).

A solution of the E form of the syn isomer of 2--benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)acetamido]-8-oxo-5-thia-1-azabicyclo[4.2.0]oct-2-ene-5-oxide (8.5 g) and dimethylacetamide (3 cc) in methylene chloride (100 cc) is treated with phosphorus trichloride (1.40 cc) at −10° C., whilst stirring; after 1 hour 30 minutes and then after 2 hours, phosphorus trichloride is added (0.7 cc each time). The mixture is diluted with ethyl acetate (600 cc), the resulting mixture is washed with a 2% strength solution of sodium bicarbonate (2×150 cc) and a semi-saturated solution of sodium chloride (2×150 cc), dried over sodium sulphate and filtered and the filtrate is concentrated to dryness at 20° C. under a pressure of 20 mm Hg (2.7 kPa). The residue is taken up in ethyl acetate (50 cc) and the solution is chromatographed on a column of Merck silica gel (0.05–0.2) (100 g) (diameter of the column: 3 cm, height: 25 cm). Elution is carried out with ethyl acetate (1 liter), 200 cc fractions being collected. Fractions 3, 4 and 5 are concentrated to dryness (20 mm Hg; 2.7 kPa) at 20° C. The E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)acetamido]-8-oxo-5-thia-1-azabicyclo[4.2.0]oct-2-ene (7.5 g) is collected in the form of a hard orange foam.

Infra-red spectrum (CHBr$_3$), characteristic bands (cm$^{-1}$): 3,380, 1,780, 1,720, 1,680, 1,515, 1,490, 1,445, 755, 740.

Proton NMR spectrum (350 MHz, CDCl$_3$, δ in ppm, J in Hz): 3.40 (s, 6H, —OCH$_3$); 3.54 and 3.66 (2d, J=18, 2H, —SCH$_2$—); 3.98 (d, J=5, 2H, >NCH$_2$—); 4.02 (s, 3H, =NOCH$_3$); 4.65 (t, J=5, 1H, —CH(OCH$_3$)$_2$); 5.08 (d, J=4, 1H, H in the 6-position); 5.92 (dd, J=4 and 9, 1H, H in the 7-position); 6.73 (s, 1H, H of the thiazole); 6.83 (d, J=16, 1H, —CH=CHS—);

6.95 (s, 1H, —COOCH—).
            |

(a) A solution of the E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)acetamido]-8-oxo-5-thia-1-azabicyclo[4.2.0]oct-2-ene (1.05 g) in 98% strength formic acid (20 cc) is heated at 50° C. for 30 minutes. The mixture is concentrated to dryness at 50° C. under a pressure of 0.05 mm Hg (0.007 kPa), the residue is taken up in acetone (50 cc), the mixture is concentrated to dryness at 30° C. under reduced pressure (20 mm Hg; 2.7 kPa) and this operation is repeated a second time.

The solid obtained is treated with acetone (50 cc) at 60° C., for 10 minutes, whilst stirring, the cooled suspension is filtered, the residue is dried and the E form of the syn isomer of 7-[2-(2-aminothiazol-4-yl)-2-methoxyiminoacetamido]-2-carboxy-3-{2-[5,6-dioxo-4-formylmethyl-1,4,5,6-tetrahydro-1,2,4-triazin-3-yl]thiovinyl}-8-oxo-5-thia-1-azabicyclo[4.2.0]oct-2-ene (0.51 g) is obtained.

Infra-red spectrum (KBr), characteristic bands (cm$^{-1}$): 3,500, 2,300, 1,770, 1,715, 1,680, 1,540, 1,050, 950.

Proton NMR spectrum (350 MHz, CF$_3$COOD, δ in ppm, J in Hz): 3.87 (limiting AB-type, 2H, —SCH$_2$—); 4.30 (s, 3H, —OCH$_3$); 5.20 (s broad, 2H, >NCH$_2$—); 5.38 (d, J=4, 1H, H in the 6-position); 6.03 (d, J=4, 1H, H in the 7-position); 7.22 (d, J=16, 1H, —CH=CHS—); 7.50 (s, 1H, H of the thiazole); 7.72 (d, J=16, 1H, =CHS—); 9.74 (s broad, 1H, —CHO).

Proton NMR spectrum (350 MHz, CF$_3$COOD+D$_2$O, δ in ppm, J in Hz): 3.82 (limiting AB-type, 2H, —SCH$_2$—); 4.26 (s, 3H, —OCH$_3$); 5.10 (s broad, 2H, >NCH$_2$—); 5.31 (d, J=4, 1H, H in the 6-position); 5.96 (d, J=4, 1H, H in the 7-position); 7.06 (d, J=16, 1H, —CH=CHS—); 7.43 (s, 1H, H of the thiazole); 7.56 (d, J=16, 1H, =CHS—); 9.67 (s broad, 1H, —CHO).

(b) The following procedure can also be used:

A mixture of the E form of the syn isomer of 2-benzhydryloxycarbonyl-3-{2-[4-(2,2-dimethoxyethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (1 g), pure formic acid (40 cc), water (1.27 cc) and Merck silica gel (0.05–0.2) (6 g) is heated at 50° C., for 30 minutes and whilst stirring. It is concentrated to dryness at 30° C. under 20 mm Hg (2.7 kPa) and the powder obtained is deposited on a column of Merck silica gel (0.05–0.2) (20 g) (diameter of the column: 2 cm, height: 17 cm). Elution is carried out with a 3/1/1 (by volume) mixture of ethyl acetate, formic acid and water, 10 cc fractions being collected. Fractions 3 to 26 are concentrated to dryness at 27° C. under 0.05 mm Hg (0.007 kPa). The yellow solid obtained is triturated in ether (60 cc), the mixture is filtered, the residue is dried and the E form of the syn isomer of 7-[2-(2-aminothiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (0.4 g) is obtained, the NMR and infra-red characteristics of which are identical to those of the product prepared in accordance with (a).

(c) A mixture of the E form of the syn isomer of 7-[2-(2-aminothiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (0.297 g), water (10 cc) and sodium bicarbonate (0.042 g) is stirred, under nitrogen, until the solids have dissolved, and the solution is filtered and lyophilised. The sodium salt of the aldehyde hydrate of the E form of the syn isomer of 7-[2-(2-aminothiazol-4-yl)-2-methoxyiminoacetamido]-2-carboxy-3-[2-(5,6-dioxo-4-formylmethyl-1,4,5,6-tetrahydro-1,2,4-triazin-3-yl)-thiovinyl]-8-oxo-5-thia-1-azabicyclo[4.2.0]oct-2-ene (0.28 g) is collected.

Infra-red spectrum (KBr), characteristic bands in cm$^{-1}$: 3,420, 3,200, 1,760, 1,710, 1,670, 1,600, 1,530, 1,040, 945.

Proton NMR spectrum (350 MHz, DMSO-d$_6$+D$_2$O, δ in ppm, J in Hz): 3.54 (limiting AB-type, 2H, —SCH$_2$—); 5.06 (d, J=4, 1H, H in the 6-position); 5.08 (s, 1H, —CH(OH)$_2$); 5.63 (d, J=4, 1H, H in the 7-position); 6.44 (d, J=16, 1H, —CH=CHS—); 6.76 (s, 1H, H of the thiazole); 7.24 (d, J=16, 1H, =CHS—); 9.60 (s, 0.05H, —CHO).

The NMR spectrum of this sodium salt of the aldehyde hydrate, run in CF$_3$COOD, shows that, in solution in this solvent, the product is in the aldehyde form [spectrum identical to that described above under (a)].

REFERENCE EXAMPLE C

The product of Example 3 can be used in the following manner:

A mixture of the E form of 7-amino-2-benzhydryloxycarbonyl-8-oxo-3-(2-tosyloxyvinyl)-5-thia-1-azabicyclo[4.2.0]oct-2-ene-5-oxide (0.614 g), dimethylformamide (50 cc) and the syn isomer of 4-(2-t-butoxycarbonylaminoethyl)-5,6-dioxo-3-[2-methoxyimino-2-(2-tritylaminothiazol-4-yl)-acetylthio]-1,4,5,6-tetrahydro-1,2,4-triazine (0.70 g) is heated at 60° C. for 6 hours under nitrogen. The mixture is diluted with ethyl acetate (150 cc), the resulting mixture is washed with water (2×120 cc), 1 N hydrochloric acid (2×100 cc), water (100 cc) and water saturated with sodium chloride (100 cc), dried over sodium sulphate and filtered and the filtrate is concentrated to dryness at 20° C. under 20 mm Hg (2.7 kPa). The residue is chromatographed on a column of Merck silica gel (0.06–0.2) (40 g) (diameter of the column: 2.5 cm, height: 29 cm). Elution is carried out with ethyl acetate (1 liter), 60 cc fractions being collected. Fractions 3 to 6 are concentrated to dryness at 20° C. under 20 mm Hg (2.7 kPa). The E form of the syn isomer of 2-benzhydryloxycarbonyl-3-{2-[4-(2-t-bu toxycarbonylaminoethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene-5-oxide (0.21 g) is collected in the form of a hard brown foam.

Infra-red spectrum (KBr), characteristic bands (cm$^{-1}$): 3,380, 1,795, 1,715, 1,690, 1,590, 1,520, 1,495, 1,445, 1,205, 1,160, 1,040, 940, 750, 700.

Proton NMR spectrum (350 MHz, CDCl$_3$, δ in ppm, J in Hz): 1.36 (s, 9H, —C(C$\underline{H}_3$)$_3$); 3.30 and 4.65 (2d, J=18, 2H, —SCH$_2$—); 3.38 (m, 2H, —C$\underline{H}_2$NHCO—); 3.95 (m, 2H, —CH$_2$—C$\underline{H}_2$NH—); 4.0 (s, 3H, CH$_3$ON=); 5.20 (d, J=4, H$_6$); 6.03 (dd, J=4 and 9, H$_7$); 6.70 (s, H of the thiazole); 6.86 (d, J=16, —C$\underline{H}$=C-HS—); 6.94 (s, —COOC$\underline{H}$<); 11.7 (s broad, —NH—triazine).

A solution of the E form of the syn isomer of 2-benzhydryloxycarbonyl-3-{2-[4-(2-t-butoxycarbonylam inoethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.-0]oct-2-ene-5-oxide (3.36 g) in methylene chloride (30 cc) and dimethylacetamide (1.2 cc) is treated, at −10° C., for 1 hour 30 minutes, whilst stirring, with phosphorus trichloride (1.04 cc). The mixture is diluted with ethyl acetate (250 cc), the resulting mixture is washed with a 2% strength solution of sodium bicarbonate (150 cc) and water semi-saturated with sodium chloride (2×100 cc), dried over sodium sulphate and filtered and the filtrate is concentrated to dryness at 20° C. under 20 mm Hg (2.7 kPa). The product is fixed onto Merck silica gel (0.06–0.2) (5 g) and chromatographed on a column of Merck silica gel (0.06–0.2) (50 g) (diameter of the column: 3 cm, height: 15 cm). Elution is carried out with ethyl acetate (6 liters), 600 cc fractions being collected. Fractions 2 to 7 are concentrated to dryness at 20° C. under 20 mm Hg (2.7 kPa) and the E form of the syn isomer of 2-benzhydryloxycarbonyl-3-{2-[4-(2-t-bu toxycarbonylaminoethyl)-5,6-dioxo-1,4,5,6-tetrahydro-1,2,4-triazin-3-yl]-thiovinyl}-7-[2-methoxyimino-2-(2-tritylaminothiazol-4-yl)-acetamido]-8-oxo-5-thia-1-azabicyclo[4.2.0]oct-2-ene (1.97 g) is collected in the form of a hard yellow foam.

Infra-red spectrum (KBr), characteristic bands (cm$^{-1}$): 3,400, 3,280, 1,790, 1,715, 1,695, 1,590, 1,520, 1,495, 1,450, 1,040, 945, 755, 700.

Proton NMR spectrum (350 MHz, DMSO, δ in ppm, J in Hz): 1.33 (s, 9H, —C(C$\underline{H}_3$)$_3$; 3.20 (m, 2H, —CH$_2$C$\underline{H}_2$N<); 3.64 and 3.86 (2d, J=18, 2H, —SCH$_2$—); 3.83 (t, J=6, 2H, —CH$_2$—C$\underline{H}_2$N<); 3.84 (s, 3H, =NOC$\underline{H}_3$); 5.25 (d, J=4, 1H, H$_6$); 5.77 (dd, J=4 and 9, 1H, H$_7$); 6.72 (s, 1H, H of the thiazole); 6.92 (s, 1H, —COOC$\underline{H}$<); 9.93 and 7.02 (2d, J=12, 2H, —CH=CH—S—); 8.82 (s, 1H, —NH—); 9.58 (d, J=9, 1H, —NHCO—); 12.55 (s, 1H, —NH—triazine).

A mixture of the E form of the syn isomer of 2-benzhydryloxycarbonyl-3-{2-[4-(2-t-butoxycarbonylam inoethyl)-5,6-dioxo-1,4,5,6-tetrahydro-1,2,4-triazin-3-yl]-thiovinyl}-7-[2-methoxyimino-2-(2-tritylamino-thiazol-4-yl)-acetamido]-8-oxo-5-thia-1-azabicyclo[4.2.-0]oct-2-ene (1.88 g), formic acid (35 cc) and water (15 cc) is heated at 50° C. for 30 minutes. Water (20 cc) is then added, the mixture is left to cool to 20° C. and filtered and the filtrate is concentrated to dryness at 50° C. under 0.05 mm Hg (0.007 kPa). The residue is taken up in ethanol (2×100 cc), the mixture being concentrated to dryness each time at 20° C. under 20 mm Hg (2.7 kPa). The residue is treated with ethanol (50 cc) at 45° C. for 15 minutes, the mixture is filtered and the solid is washed with ether (2×20 cc) and dried. The formate of the E form of the syn isomer of 7-[2-(2-am inothiazol-4-yl)-2-methoxyiminoacetamido]-3-{2-[4-(2-aminoethyl)-5,6-dioxo-1,4,5,6-tetrahydro-1,2,4-triazin-3-yl]-thiovinyl}-2-carboxy-8-oxo-5-thia-1-azabicy-clo[4.2.0]oct-2-ene (1.08 g) is collected in the form of a yellow powder.

Infra-red spectrum (KBr), characteristic bands (cm$^{-1}$): 3,500, 2,200, 1,770, 1,710, 1,680, 1,630, 1,530, 1,380, 1,040, 930.

Proton NMR spectrum (350 MHz, DMSO, δ in ppm, J in Hz): 3.12 (m, 2H, —CH$_2$—C$\underline{H}_2$—NH$_2$); 3.51 and 3.60 (2d, J=18, 2H, —SCH$_2$—); 3.85 (s, 3H, CH$_3$ON=); 4.12 (t, J=6, 2H, >NC$\underline{H}_2$—CH$_2$—NH$_2$); 5.12 (d, J=4, 1H, H$_6$); 5.67 (dd, J=4 and 9, 1H, H$_7$); 6.44 (d, J=8, 1H, —C$\underline{H}$=CHS—); 6.73 (s, 1H, H of the thiazole); 7.2 (s broad, 2H, —NH$_2$); 8.18 (s, 1H, H of the formate); 9.55 (d, J=9, 1H, —NHCO—).

REFERENCE EXAMPLES (D) TO (AV)

By following an analogous procedure, the thioloesters according to the invention can be used for the preparation of the products of the general formula:

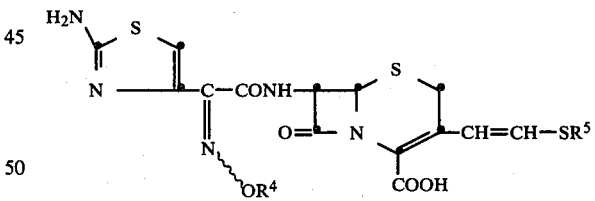

which are identified below:

| Reference Example | R$^5$ | R$^4$ | Stereo-chemistry | (1) IR spectrum (KBr), characteristic bands in cm$^{-1}$ (2) Proton NMR spectrum, 350 MHz, DMSO-d$_6$, δ in ppm, J in Hz |
| --- | --- | --- | --- | --- |

| | | | | |
|---|---|---|---|---|
| D | 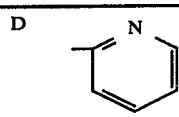 | —CH₃ | syn isomer, E form | (1) 3,500, 2,820, 2,600, 1,775, 1,670, 1,650, 1,630, 1,575, 1,450, 1,415, 1,380, 1,040, 940, 765<br>(2) 3.72 and 3.95 (2d, J = 18, 2H, H in the 4-position); 3.85 (s, 3H, —OCH₃); 5.20 (d, J = 4, 1H, H in the 6-position); 5.77 (dd, J = 4 and 9, 1H, H in the 7-position); 6.76 (s, 1H, H of the thiazole); 7.15 (d, J = 17, 1H, —CH=CHS—); 7.18 (s, 2H, amino); 7.44 (d, J = 16, 17, —CH=CHS—); 7.75 and 8.2 (d, t, 1H, J = 8, H in the 4-position of the pyridine); 8.50 (t, 1H, J = 4, H₂ of the pyridine); 9.50 (d, J = 9, 1H, —CONH—). |
| E | 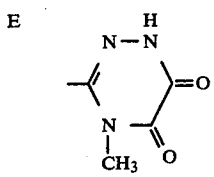 | —CH₃ | syn isomer, E form | (1) 3,300, 3,260, 2,600, 1,770, 1,705, 1,680, 1,630, 1,585, 1,530, 1,375, 1,040, 950<br>(2) 3.35 (s, 3H, —CH₃ triazine); 3.65 and 3.88 (AB - type, J = 18, 2H, —SCH₂—); 3.87 (s, 3H, =NOCH₃); 5.22 (d, J = 4, 1H, H in the 6-position); 5.80 (dd, J = 4 and 9, 1H, H in the 7-position); 6.75 (s, 1H, H of the thiazole); 6.83 (d, J = 16, —CH=CH—S—); 7.11 (d, J = 16, 1H, —CH=CH—S—); 7.20 (s broad, 3H, —NH₃⁺); 9.58 (d, J = 9, 1H, —CONH—). |
| F | 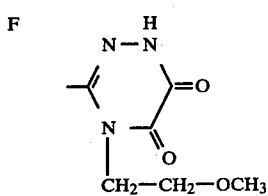 | —CH₃ | syn isomer, E form | (1) 3,480, 2,830, 1,775, 1,710, 1,680, 1,635, 1,590, 1,535, 1,380, 1,110, 1,040, 940<br>(2) 3.36 (s, 3H, —CH₂OCH₃); 3.56 (t, J = 5, 2H, —CH₂O—); 4.10 (t, J = 5, 2H, —CH₂N⟨); 3.62 and 3.73 (2d, J = 18, 2H, —SCH₂—); 3.96 (s, 3H, =NOCH₃); 5.18 (d, J = 4, 1H, H in the 6-position); 5.81 (dd, J = 4 and 9, 1H, H in the 7-position); 6.78 (s, 1H, H of the thiazole); 6.87 (d, J = 15, 1H, —CH=CH—S—); 7.29 (d, J = 15, 1H, —CH=CH—S—); 6.70 (s broad, 3H, —NH₃⁺); 9.55 (d, J = 9, 1H, —CONH—); 12.64 (s, 1H, —OH). |
| G | 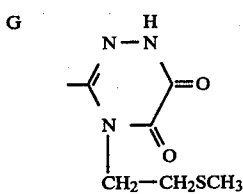 | —CH₃ | syn isomer, E form | (1) 3,600, 2,200, 1,770, 1,710, 1,680, 1,585, 1,535, 1,040, 945<br>(2) 2.12 (s, 3H, —SCH₃); 2.73 (t, J = 7, 2H, —CH₂S—CH₃); 3.64 and 3.82 (2d, J = 18, 2H, —SCH₂—); 3.85 (s, 3H, —OCH₃); 4.0 (t, J = 7, 2H, ⟩NCH₂—); 5.20 (d, J = 4, 1H, H in the 6-position); 5.78 (dd, J = 4 and 9, 1H, H in the 7-position); 6.73 (s, 1H, H of the thiazole); 6.92 (d, J = 16, 1H, —CH=CHS—); 7.12 (d, J = 16, 1H, =CHS—); 7.15 (s, 3H, —NH₃⁺); 9.66 (d, J = 9, 1H, —CONH—); 12.61 (s, 1H, ⟩NNHCO—). |
| H | 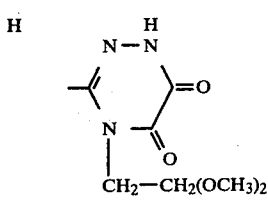 | —CH₃ | syn isomer, E form | (1) 3,500, 3,300, 1,780, 1,715, 1,680, 1,590, 1,535, 1,050, 950<br>(2) 3.62 and 3.81 (2d, J = 18, —SCH₂—); 3.84 (s, 3H, —OCH₃); 3.97 (d, J = 3, 2H, ⟩NCH₂—); 4.58 (t, J = 3; 1H, —CH(OCH₃)₂); 5.20 (d, J = 4, 1H, H in the 6-position); 5.77 (dd, J = 4 and 9, 1H, H in the 7-position); 6.74 (s, 1H, H of the thiazole); 6.91 (d, J = 16, 1H, —CH=CHS—); 7.09 (d, J = 16, 1H, =CHS—); 7.17 (s, 3H, —NH₃⁺); 9.60 (d, J = 9, 1H, —CONH—); 12.64 (s, 1H, =NNHCO—). |

-continued

| | | | | |
|---|---|---|---|---|
| I | 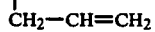 | —CH₃ | syn isomer, E form | (1) 3,600, 2,300, 1,775, 1,710, 1,680, 1,535, 1,040, 945<br>(2) 3.63 and 3.80 (2d, J = 18, 2H, —SCH₂—); 3.88 (s, 3H, —OCH₃); 4.48 (d, J = 4, 2H, ⟩NCH₂—); 5.19 to 5.27 (mt, 3H, =CH₂ and H in the 6-position); 5.74 to 5.92 (mt, 2H, —CH=CH₂ and H in the 7-position); 6.74 (s, 1H, H of the thiazole); 6.91 (d, J = 16, 1H, —CH=CHS—); 7.09 (d, J = 16, 1H, =CHS—); 7.18 (s, —NH₃⁺); 9.60 (d, J = 9, 1H, —CONH—); 12.61 (s, 1H, =N—NHCO— or =N—N=C—).<br>                                                   OH |
| Reference Example | R⁵ | R⁴ | Stereochemistry | (1) IR spectrum (KBr), characteristic bands in cm⁻¹<br>(2) Proton NMR spectrum, 350 MHz, DMSO-d₆ + D₂O, δ in ppm, J in Hz |
| J |  | —CH₃ | syn isomer, E form | Product containing about 25% of the formate of one or other of the —OH groups<br>(1) 3,650–2,200, 1,770, 1,710, 1,680, 1,590, 1,530, 1,045, 945<br>(2) diol: 3.87 (s, 3H, =NOCH₃); 5.20 (d, J = 4, 1H, H in the 6-position); 5.75 (d, J = 4, 1H, H in the 7-position); 6.74 (s, 1H, H of the thiazole); 6.95 and 7.10 (2d, J = 16, 2H, —CH=CH—S—)<br>formate: 3.87 (s, 3H, =NOCH₃); 5.18 (d, J = 4, 1H, H in the 6-position); 5.75 (d, J = 4, 1H, H in the 7-position); 6.74 (s, 1H, H of the thiazole); 6.93 and 7.08 (2d, J = 16, 2H, —CH=CHS—); 8.22 (s, 1H, —HCOO⁻) |
| Reference Example | R⁵ | R⁴ | Stereochemistry | (1) IR spectrum (KBr), characteristic bands in cm⁻¹<br>(2) Proton NMR spectrum, 350 MHz, DMSO-d₆, δ in ppm, J in Hz |
| K |  | —CH₃ | syn isomer, E form | (2) 3.60 (t, J = 5, 2H, ⟩N—CH₂—CH₂OH); 3.84 (s, 3H, =NOCH₃); 3.92 (t, J = 5, 2H, ⟩N—CH₂CH₂OH); 5.10 (d, J = 4, 1H, H in the 6-position); 5.65 (dd, J = 4 and 9, 1H, H in the 7-position); 6.39 (d, J = 16, 1H, —CH=CH—S—); 6.73 (s, 1H, H in the 5-position of the thiazole); 7.17 (s broad, 2H, —NH₂); 7.37 (d, J = 16, 1H, —CH=CH—S—); 9.54 (d, J = 9, 1H, —CONH—C₇). |
| L |  | —CH₃ | syn isomer, E form | (1) 3,500, 2,500, 1,775, 1,710, 1,685 to 1,630, 1,540, 1,045, 950<br>(2) 1.90 (s, 3H, —CH₃); 3.48 (m, 2H, —CH₂NH—); 3.62 and 3.73 (2d, J = 18, 2H, —SCH₂—); 4.0 (s, 3H, —OCH₃); 5.15 (d, J = 4, 1H, H in the 6-position); 5.82 (dd, J = 4 and 9, 1H, H in the 7-position); 6.78 (s, 1H, H of the thiazole); 6.86 (d, J = 16, 1H, —CH=CHS—); 7.31 (d, J = 16, 1H, =CHS—); 7.73 (s, 3H, —NH₃⁺); 9.50 (d, J = 9, 1H, —CONH—); 12.54 (s broad, 1H, —CONHN= or —C=N—N=).<br>                                   OH |

-continued

| | | | | |
|---|---|---|---|---|
| M | ![structure: N-methyl triazole with COOCH3]  CH3 on N, triazole ring with COOCH3 | —CH3 | syn isomer, E form | (1) 3,450, 3,320, 2,200, 1,770, 1,735, 1,660, 1,630, 1,535, 1,385, 1,220, 1,040, 945<br>(2) 3.66 and 3.90 (2d, J = 18, 2H, —SCH2—); 3.85 (s, 3H, =NOCH3); 3.87 (s, 3H, —CO2CH3); 3.90 (s, 3H, >NCH3 triazole); 5.20 (d, J = 9, 1H, H in the 6-position); 5.79 (dd, J = 4 and 9, 1H, H in the 7-position); 6.74 (s, 1H, H thiazole); 6.98 and 7.03 (AB-type, J = 14, 2H, —CH=CH—S—); 7.20 (s broad, 2H, —NH2); 9.63 (d, J = 9, 1H, —CONH—C7). |
| N | thiazole—CH2NHCOCH3 | —CH3 | syn isomer, E form | (1) 3,320, 1,770, 1,660, 1,540, 1,380, 1,040<br>(2) 1.90 (s, 3H, —COCH3); 3.68 and 3.92 (2d, J = 18, 2H, —SCH2—); 3.87 (s, 3H, —OCH3); 4.22 (d, J = 4, 1H, H in the 6-position); 4.60 (limiting AB-type, 2H, —CH2NHCO—); 5.82 (dd, J = 4 and 9, 1H, H in the 7-position); 6.75 (s, 1H, —OCH3); 7.15 (d, J = 16, 1H, —CH=CHS—); 7.20 (s, 3H, —NH3+); 7.25 (d, J = 16, 1H, =CHS—); 9.63 (d, J = 9, 1H, —CONH—). |
| O | thiazole—CH2N(CH3)2 | —CH3 | syn isomer, E form | (2) 2.36 (s, 6H, —N(CH3)2); 3.67 and 3.92 (AB-type, J = 18, 2H, —SCH2—); 3.88 (s, 3H, =NOCH3); 5.20 (d, J = 4, 1H, H in the 6-position); 5.80 (dd, J = 4 and 9, 1H, H in the 7-position); 6.76 (s, 1H, H thiazole); 7.10 and 7.25 (2d, J = 16, 2H, —CH=CH—S—); 7.20 (s broad, 2H, —NH2); 9.60 (d, J = 9, 1H, —CONH—). |
| P | triazole with CH2CH2OH on N | —CH3 | syn isomer, E form | (1) 3,350, 1,770, 1,720, 1,675, 1,530, 1,390, 1,040, 940<br>(2) 3.63 and 3.87 (AB-type, J = 19, 2H, —SCH2—); 3.77 and 4.41 (2t, 4H, —CH2CH2O—); 3.84 (s, 3H, —OCH3); 5.19 (d, J = 4, 1H, H in the 6-position; 5.89 (dd, J = 4 and 9, 1H, H in the 7-position); 6.73 (s, 1H, H in the 5-position of the thiazole); 6.94 (d, J = 16, 1H, —CH=CHS—); 7.25 (d, J = 16, 1H, =CHS—); 9.61 (d, J = 9, 1H, —CONH—). |
| Q | triazole with CH2CH2NH—CO—CH3 on N | —CH3 | syn isomer, E form | (1) 3,500, 2,500, 1,775, 1,660, 1,540, 1,040, 945<br>(2) 1.90 (s, 3H, —CH3); 3.44 (t, 2H, >NCH2—); 3.60 (q, 2H, —CH2NHCO—); 3.64 and 3.76 (2d, J = 18, 2H, —SCH2—); 4.0 (s, 3H, —OCH3); 5.16 (d, J = 4, 1H, H in the 6-position); 5.82 (dd, J = 4 and 9, 1H, H in the 7-position); 6.60 (s, 3H, —NH3+); 6.78 (s, 1H, H of the thiazole); 6.96 (d, J = 16, 1H, —CH=CHS—); 7.37 (d, J = 16, 1H, =CHS—); 7.86 (t, J = 5, 1H, —NHCOCH3); 9.50 (d, J = 9, 1H, —CONH—). |
| R | triazole with CH2CH2N(CH3)2 on N | —CH3 | syn isomer, E form | (1) 2,820, 1,770, 1,670, 1,530, 1,610, 1,385, 1,030<br>(2) 2.70 (s, 6H, —N(CH3)2); 2.75 and 3.95 (2t, J = 7, 4H, —CH2CH2—); 3.85 (s, 3H, =NOCH3); 5.16 (d, J = 4, 1H, H in the 6-position); 5.85 (dd, J = 4 and 9, 1H, H in the 7-position); 6.8 and 6.9 (2d, J = 16, 2H, —CH=CH—S—); 9.63 (d, J = 9, 1H, —CONH—); 7.20 (s broad, 2H, —NH2 thiazole). |

| | | | | |
|---|---|---|---|---|
| S | 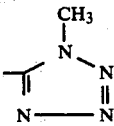 | —CH₃ | syn isomer, Z form | Product in the form of the trifluoroacetate<br>(1) 3,300, 1,785, 1,675, 1,180, 1,140, 1,050<br>(2) 3.8 and 3.85 (AB-type, J = 17.5, 2H, —SCH₂—); 3.93 (s, 3H, >NCH₃); 4.0 (s, 3H, —OCH₃); 5.26 (d, J = 4, 1H, H in the 6-position); 5.85 (dd, J = 4 and 10, H in the 7-position); 6.75 (d, J = 11, 1H, —CH=CHS—); 6.87 (s, 1H, H in the 5-position of the thiazole); 6.91 (d, J = 11, 1H, =CHS—); 9.34 (d, J = 10, 1H, —CONH—). |
| T | 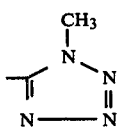 | —CH₃ | syn isomer, E form | Product in the form of the trifluoroacetate<br>(1) 3,320, 1,780, 1,675, 1,200, 1,140, 1,040, 950<br>(2) 3.66 and 3.86 (2d, J = 17, —SCH₂—); 3.90 (s, 3H, >NCH₃); 4.0 (s, 3H, —OCH₃); 5.20 (d, J = 4, 1H, H in the 6-position); 5.80 (dd, J = 4 and 9, 1H, H in the 7-position); 6.83 (s, 1H, H in the 5-position of the thiazole); 7.0 (d, J = 16, 1H, —CH=CHS—); 7.1 (d, J = 16, 1H, =CHS—); 9.7 (d, J = 9, 1H, —CONH—). |
| U | 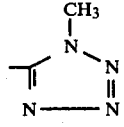 | —OH | syn isomer, E form | (1) 3,440, 3,360, 3,200, 1,785, 1,720, 1,680, 1,610, 1,405<br>(2) 3.65 and 3.91 (2d, J = 18, 2H, —SCH₂—); 4.97 (s, 3H, >NCH₃); 5.25 (d, J = 4, 1H, H in the 6-position); 5.90 (dd, J = 4 and 9, 1H, H in the 7-position); 6.76 (s, 1H, H in the 5-position of the thiazole); 6.96 (d, J = 14, 1H, —CH=CHS—); 7.07 (d, J = 14, 1H, =CHS—); 9.50 (d, J = 9, 1H, —CONH—). |
| V | 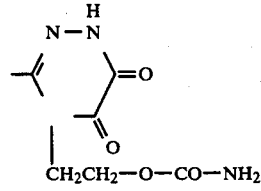 | —CH₃ | syn isomer, E form | (1) 3,550, 2,200, 1,770, 1,710, 1,680, 1,050, 940<br>(2) 3.62 and 3.82 (2d, J = 18, 2H, —SCH₂—); 3.86 (s, 3H, =NOCH₃); 4.06 and 4.15 (2t, J = 5, 2 × 2H, >NCH₂CH₂O—); 5.21 (d, J = 9, 1H, H in the 6-position); 5.78 (dd, J = 4 and 9, 1H, H in the 7-position); 6.50 (s broad, 2H, —OCONH₂); 6.75 (s, 1H, H of the thiazole); 6.92 and 7.08 (2d, J = 16, 2H, —CH=CH—S—); 7 to 7.50 (s broad, 2H, —NH₂ thiazole); 9.66 (d, J = 9, 1H, —CONH—C₇); 12.62 (s, 1H, —N=C—OH triazine). |
| W | 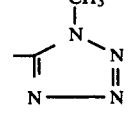 | —CH=CH₂ | syn isomer, E form | (1) 3,340, 1,770, 1,680, 1,620, 1,530 and 1,380<br>(2) 3.64 and 3.89 (2d, J = 18, 2H —SCH₂—); 4.0 (s, 3H, —CH₃), 4.22 (dd, J = 2 and 6, 1H, 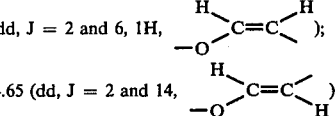); 4.65 (dd, J = 2 and 14, 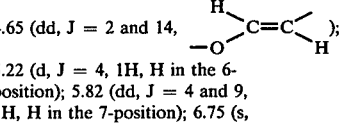); 5.22 (d, J = 4, 1H, H in the 6-position); 5.82 (dd, J = 4 and 9, 1H, H in the 7-position); 6.75 (s, 1H, H of the thiazole); 6.95 (d, J = 16, 1H, —CH=CHS—); 6.96 (dd, J = 6 and 14, 1H, —OCH=CH₂); 7.13 (d, J = 16, 1H, =CHS—); 9.83 (d, J = 9, 1H, —CONH—) |

| | | | | |
|---|---|---|---|---|
| X | 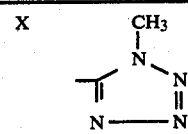 | —CH₂CN | syn isomer, E form | (1) 1,770, 1,680, 1,620, 1,530, 1,380<br>(2) 3.66 and 3.88 (2d, J = 18, 2H, —SCH₂—); 4.02 (s, 3H, —CH₃); 5.0 (s, 2H, —OCH₂—); 5.22 (d, J = 4, 1H, H in the 6-position); 5.80 (dd, J = 4 and 9, 1H, H in the 7-position); 6.89 (s, 1H, H of the thiazole); 6.99 (d, J = 16, 1H, —CH=CHS—); 7.12 (d, J = 16, 1H, =CHS—); 9.82 (d, J = 9, 1H, —CONH—) |
| Y | 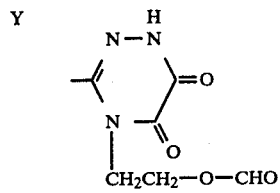 | —CH₃ | syn isomer, E form | (1) 3,400, 3,200, 2,200, 1,775, 1,710, 1,680, 1,530, 1040, 945<br>(2) 3.62 and 3.82 (AB-type, J = 18, 2H, —SCH₂—); 3.84 (s, 3H, =NOCH₃); 4.15 and 4.32 (2t, J = 5, 2 × 2H, >NCH₂CH₂—OCHO); 5.21 (d, J = 4, 1H, H in the 6-position); 5.78 (dd, J = 4 and 9, 1H, H in the 7-position); 6.73 (s, 1H, H of the thiazole); 6.89 and 7.10 (2d, J = 16, 2H, —CH=CH—S—); 7.16 (s broad, 2H, —NH₂); 8.18 (s, 1H, HCOO—); 9.59 (d, J = 9, 1H, —CONH—C₇); 12.60 (s broad, 1H, —N=COH triazine). |
| Z | 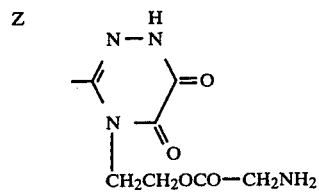 | —CH₃ | syn isomer, E form | (1) 3,550, 2,200, 1,755, 1,705, 1,675, 1,580, 1,530, 1,035<br>(2) 3.51 and 3.62 (AB-type, J = 18, 2H, —SCH₂—); 3.72 (mt, 2H, —COCH₂NH₂); 3.82 (s, 3H, =NOCH₃); 4.12 and 4.40 (2 Mt, 2 × 2H, >NCH₂CH₂OCO—); 5.10 (d, J = 4, 1H, H in the 6-position); 5.67 (dd, J = 4 and 9, 1H, H in the 7-position); 6.44 (d, J = 16, 1H, —CH=CH—S); 6.72 (s, 1H, H of the thiazole); 7.18 (s broad, 3H, —NH₃⁺ thiazole); 8.12 (s, 1H, HCO₂⁻); 9.56 (d, J = 9, 1H, —CONH—C₇). |
| AA | 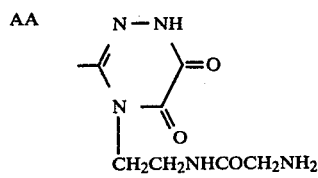 | —CH₃ | syn isomer, E form | Product obtained as the formate.<br>(1) 3,700 to 2,200, 1,765, 1,705, 1,675, 1,610, 1,585, 1,530, 1,035, 930<br>(2) 3.2 to 3.6 (m, 8H, —SCH₂—, >NCH₂CH₂N< and —COCH₂N<); 3.85 (s, =NOCH₃); 5.12 (d, J = 4, H₆); 5.67 (dd, J = 4 and 9, H₇); 6.35 (d, J = 16, —CH=CHS—); 6.73 (s, H of the thiazole); 7.15 (s broad, —NH₂); 8.2 (s, H of the formate); 8.6 (m, —CH₂NHCO—); 9.54 (d, J = 9, —NHCO—) |
| AB | 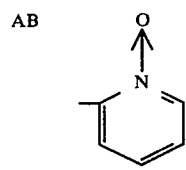 | —CH₃ | syn isomer, E form | (1) 3,330, 1,770, 1,670, 1,540, 1,470, 1,420, 1,040, 950, 760<br>(2) 3.75 and 4.16 (AB-type, J = 18, 2H, —SCH₂—); 3.88 (s, 3H, =NOCH₃); 5.24 (d, J = 4, 1H, H in the 6-position); 5.73 (dd, J = 4 and 9, 1H, H in the 7-position); 6.78 (s, 1H, H of the thiazole); 7.05 and 7.32 (AB-type, J = 16, 2H, —CH=CH—S—); 7.63 (d, J = 7, 1H, H in the 3-position of the pyridine); 7.1 to 7.5 (hump, 4H, H in the 4- and 5-position of the pyridine + —NH₂); 7.63 (d, J = 7, 1H, H in the 3-position of the pyridine); 8.32 (d, J = 6, 1H, H in the 6-position of the pyridine); 9.64 (d, J = 9, 1H, —CONH—). |

-continued

| Ref. Ex. | Structure | | Stereo- | Spectra |
|---|---|---|---|---|
| AC | (pyrimidine ring with two N) | —CH₃ | syn isomer, E form | (1) 3,320, 3,200, 3,100 to 2,100, 1,770, 1,665, 1,560, 1,550, 1,040, 945, 770, 750<br>(2) 3.72 and 3.90 (2d, J = 18, 2H, —SCH₂— in the 4-position); 3.86 (s, 3H, =NOCH₃); 5.20 (d, J = 4, 1H, —H in the 6-position); 5.77 (dd, J = 4 and 9, 1H, —H in the 7-position); 6.74 (s, 1H, —H of the thiazole nucleus); 7.12 and 7.46 (2d, J = 16, 2H, trans vinylic protons); 7.14 (s, 2H, —NH₂ on the thiazole nucleus); 7.27 (broad, 1H, —H in the 5-position of the pyrimidine nucleus); 8.66 (d, J = 5, 2H,—H in the 4- and 6-positions of the pyrimidine nucleus); 9.60 (d, J = 9, 1H, —CONH—) |
| AD | (pyridazine N-oxide with CH₃) | —CH₃ | syn isomer, E form | (1) 3,420, 3,320, 3,230, 1,765, 1,675, 1,620, 1,535, 1,325, 1,210, 1,040, 1,000, 810<br>(2) 2.33 (s, 3H, —CH₃); 3.70 and 3.97 (2d, J = 18, 2H, —SCH₂—); 3.86 (s, 3H, —OCH₃); 5.23 (d, J = 4, 1H, H in the 6-position); 5.81 (dd, J = 4 and 9, 1H, H in the 7-position); 6.76 (s, 1H, H of the thiazole); 7.18 to 7.20 (hump, 5H, —CH=CH— and —NH₃⁺); 7.31 and 7.86 (2d, J = 7, H of the pyridazine); 9.62 (d, J = 9, 1H, —CONH—). |
| AE | (triazinedione with CH(CH₃)₂) | —CH₃ | syn isomer, E form | (1) 3,500, 2,200, 1,775, 1,705, 1,680, 1,530, 1,050, 950<br>(2) 1.48 (d, J = 7, 6H, —CH(CH₃)₂); 3.64 and 3.82 (2d, J = 18, 2H, —SCH₂—); 3.85 (s, 3H, —OCH₃); 4.42 (mt, 1H, —CH(CH₃)₂); 5.22 (d, J = 4, 1H, H in the 6-position); 5.78 (dd, J = 4 and 9, 1H, H in the 7-position); 6.74 (s, 1H, H of the thiazole); 6.93 (d, J = 16, 1H, —CH=CHS—); 7.07 (d, J = 16, 1H, =CHS—); 7.18 (s, 3H, —NH₃⁺); 9.62 (d, J = 9, 1H, —CONH—); 12.55 (s, 1H, =NNHCO— or =N—N=C—OH). |
| AF | (triazinedione with CH₂C₆H₅) | —CH₃ | syn isomer, E form | (1) 3,500, 2,300, 1,770, 1,710, 1,680, 1,585, 1,530, 1,045, 945<br>(2) 3.58 and 3.78 (2d, J = 18, 2H, —SCH₂—); 3.88 (s, 3H, —OCH₃); 5.10 (s, 2H, >NCH₂—); 5.18 (d, J = 4, 1H, H in the 6-position); 5.78 (dd, J = 4 and 9, 1H, H in the 7-position); 6.75 (s, 1H, H of the thiazole); 6.86 (d, J = 16, 1H, —CH=CHS—); 7.05 (d, J = 16, 1H, =CHS—); 7.20 (s, 3H, —NH₃⁺); 9.60 (d, J = 9, 1H, —CONH—); 12.69 (s, 1H, =NNHCO—). |
| AG | (triazinedione with CH₂CONH₂) | —CH₃ | syn isomer, E form | (1) 3,410, 3,320, 3,200, 3,100, 2,000, 1,770, 1,710, 1,680, 1,630, 1,590, 1,380, 1,040, 945<br>(2) 3.63 and 3.83 (AB-type, J = 18, 2H, —SCH₂—); 3.87 (s, 3H, =NOCH₃); 4.45 (s broad, 2H, —CH₂CONH₂); 5.20 (d, J = 4, 1H, H in the 6-position); 5.78 (dd, J = 4 and 9, 1H, H in the 7-position); 6.75 (s, 1H, H of the thiazole); 6.90 and 7.08 (2d, J = 16, 2 × 1H, —CH=CH—S—); 7.32 (s broad, 2H, —NH₂ thiazole); 7.70 (s broad, 2H, —CONH₂); 9.60 (d, J = 9, 1H, —CONH—C₇); —N=C—OH triazine, δ > 12 ppm. |

(1) IR spectrum (KBr), characteristic bands in cm⁻¹
(2) Proton NMR spectrum, 350 MHz, CF₃COOD, -continued

| ample | R⁵ | R⁴ | chemistry | δ in ppm, J in Hz |
|---|---|---|---|---|
| AH | [N—N ring with =COOCH₃ and CH₂CH(OCH₃)₂ substituents] | —CH₃ | syn isomer, E form | (1) 3,430, 3,200, 1,775, 1,735, 1,680, 1,620, 1,535, 1,385, 1,050, 945<br>(2) 3.65 (s, 6H, —CH(OCH₃)₂); 4.21 (s, 3H, —COOCH₃); 4.29 (s, 3H, =NOCH₃); 5.38 (d, J = 4, 1H, H in the 6-position); 6.08 (d, J = 4, 1H, H in the 7-position); 7.07 and 7.95 (2d, J = 16, 2H, —CH=CHS—); 7.48 (s, 1H, H of the thiazole) |
| AI | [pyrazinedione with N—CH₃, NH] | —CH₃ | syn isomer, E form | (1) 3,600, 2,300, 1,765, 1,720, 1,670, 1,600, 1,525, 1,280, 1,075, 1,040, 930<br>(2) 3.77 and 3.88 (2d, J = 18, 2H, —SCH₂—); 4.0 (s, 3H, —CH₃); 4.30 (s, 3H, =NOCH₃); 5.41 (d, J = 4, 1H, H in the 6-position); 6.0 (d, J = 4, 1H, H in the 7-position); 7.50 (s, 1H, H of the thiazole) |
| AJ | [tetrazole with CH₂CH(OCH₃)₂] | —CH₃ | syn isomer, E form | (1) 3,350, 1,780, 1,680, 1,655, 1,620, 1,530, 1,120, 1,040, 940<br>(2) 3.61 (s, 6H, >C(OCH₃)₂); 3.92 (s broad, 2H, —SCH₂—); 4.31 (s, 3H, =NOCH₃—); 4.73 (d, J = 6, 2H, >NCH₂—); 5.0 (t, J = 6, 1H, —CH₂—CH<); 5.38 (d, J = 4, H₆); 6.05 (dd, J = 4 and 9, H₇); 7.16 and 7.88 (2d, J = 16, —CH=CH—); 7.50 (S, H of the thiazole) |

| Reference Example | R⁵ | R⁴ | Stereo-chemistry | (1) IR spectrum (KBr), characteristic bands in cm⁻¹<br>(2) Proton NMR spectrum, 350 MHz, DMSO-d₆, δ in ppm, J in Hz |
|---|---|---|---|---|
| AK | [triazine with 2 CH₃ groups] | —CH₃ | syn and anti isomers (50/50 mixture), E form | (1) 3,500, 2,300, 1,770, 1,710, 1,670, 1,575, 1,530, 1,030, 940<br>(2) syn isomer, E form<br>3.35 and 3.48 (2s, 2 × 3H, 2-CH₃ of the triazine); 3.66 and 3.90 (2d, J = 18, 2H, —SCH₂—); 3.87 (s, 3H, =NOCH₃); 5.18 (d, J = 4, 1H, H in the 6-position); 5.82 (dd, J = 4 and 9, 1H, H in the 7-position); 6.74 (s, 1H, H thiazole); 6.95 and 7.14 (2d, J = 16, 2H, —CH=CH—S—); 7.18 (s broad, 2H, —NH₂); 9.64 (d, J = 9, 1H, —CONH—).<br>anti isomer, E form<br>3.35 and 3.48 (2s, 2 × 3H, 2 CH₃ of the triazine); 3.66 and 3.90 (2d, J = 18, 2H, —SCH₂—); 3.98 (s, 3H, =NOCH₃); 5.19 (d, J = 4, 1H, H in the 6-position); 5.81 (dd, J = 4 and 9, 1H, H in the 7-position); 6.95 and 7.15 (2d, J = 16, 2H, —CH=CH—S—); 7.09 (s broad, 2H, —NH₂); 9.48 (d, J = 9, 1H, —CONH—) |
| AL | [ring with C₂H₅ and NH] | —CH₃ | syn isomer, E form | (1) 3,700, 2,200, 1,770, 1,720, 1,665, 1,630, 1,590, 1,040, 945<br>(2) 1.25 (t, J = 7, 3H, —CH₂CH₃); 3.71 and 3.88 (2d, J = 18, 2H, —SCH₂—); 3.80 to 3.90 (hump, 5H, —CH₂CH₃ and —OCH₃); 5.19 (d, J = 4, 1H, H in the 6-position); 5.75 (dd, J = 4 and 9, 1H, H in the 7-position); 6.77 (s, 1H, H of the thiazole); 7.10 (s broad, 2H, —CH=CH—); 7.20 (s, 2H, —NH₂); 9.62 (d, J = 9, 1H, —CONH—) |

| | R⁵ | R⁴ | Stereo-chemistry | (1) IR spectrum (KBr), characteristic bands in cm⁻¹<br>(2) Proton NMR spectrum, 350 MHz, CDCl₃, δ in ppm, J in Hz |
|---|---|---|---|---|
| AM | thiadiazole (S, N—N) | —CH₃ | syn isomer, E form | (1) 2,820, 1,775, 1,675, 1,630, 1,530, 1,490, 1,450, 1,370, 1,040, 750, 700<br>(2) 3.68 and 3.96 (2d, J = 18, 2H, —SCH₂—); 3.84 (s, 3H, =NOCH₃); 5.21 (d, J = 4, 1H, H in the 6-position); 5.80 (dd J = 4 and 9, 1H, H in the 7-position); 6.73 (s, 1H, H of the thiazole); 7.18 to 7.22 (hump, 4H, —NH₂— and —CH=CH—); 9.03 (d, J = 9, 1H, —CONH—); 9.60 (s, 1H, H of the thiadiazole) |
| AN | thiadiazole-NH₂ (S, N—N) | —CH₃ | syn isomer, E form | (1) 3,320, 3,200, 3,100, 2,820, 2,000, 1,770, 1,670, 1,610, 1,380, 1,040, 940<br>(2) 3.83 (s, 3H, =NOCH₃); 5.12 (d, J = 4, 1H, H in the 6-position); 5.76 (dd, J = 4 and 9, 1H, H in the 7-position); 6.74 (s, 1H, H of the thiazole); 6.95 (d, J = 16, 1H, —CH=CHS—); 7.02 (d, J = 16, 1H, =CHS—); 7.18 (s broad, 2H, —NH₂ thiazole); 7.48 (s broad, 2H, —NH₂ thiadiazole); 9.60 (d, J = 9, 1H, —CONH—) |
| AO | thiadiazole-CH₃ (S, N, N, CH₃) | —CH₃ | syn isomer, E form | (2) 2.57 (s, 3H, —CH₃); 3.65 and 3.95 (2d, J = 18, 2H, —SCH₂—); 3.86 (s, 3H, —OCH₃); 5.23 (d, J = 4, 1H, H in the 6-position); 5.82 (dd, J = 4 and 9, 1H, H in the 7-position); 6.75 (s, 1H, H of the thiazole); 7.04 (d, J = 16, 1H, —CH=CHS—); 7.36 (d, J = 16, 1H, =CHS—); 9.63 (d, J = 9, 1H, —CONH—). |

| Reference Example | R⁵ | R⁴ | Stereo-chemistry | (1) IR spectrum (KBr), characteristic bands in cm⁻¹<br>(2) Proton NMR spectrum, 350 MHz, CDCl₃, δ in ppm, J in Hz |
|---|---|---|---|---|
| AP | oxazole-CH₃ (O, N, CH₃) | —CH₃ | syn isomer, E form | (1) 3,300, 2,940, 1,770, 1,675, 1,530, 1,380, 1,040, 940, 730, 700<br>(2) 2.10 (s, 3H, —CH₃); 3.66 and 3.90 (2d, J = 18, 2H, —SCH₂—); 3.86 (s, 3H, =NOCH₃); 5.19 (d, 1H, H in the 6-position); 5.78 (dd, 1H, H in the 7-position); 6.74 (s, 1H, H of the thiazole nucleus); 7.0 (d, J = 16, 1H, —CH=CHS—); 7.14 (d, J = 16, 1H, —CH=CHS—); 7.20 (s, 2H, —NH₂); 7.94 (s, 1H, H of the oxazole nucleus); 9.72 (d, J = 9, 1H, —CONH—) |

| Reference Example | R⁵ | R⁴ | Stereo-chemistry | (1) IR spectrum (KBr), characteristic bands in cm⁻¹<br>(2) Proton NMR spectrum, 350 MHz, DMSO-d₆, δ in ppm, J in Hz |
|---|---|---|---|---|
| AQ | oxadiazole-C₆H₅ (O, N—N, C₆H₅) | —CH₃ | syn isomer, E form | (1) 3,400 to 2,000, 3,330, 1,760, 1,630, 1,540, 1,380, 1,055, 750, 710, 695<br>(2) 3.68 and 3.94 (2d, J = 18, 2H, —SCH₂—); 3.86 (s, 3H, =NOCH₃); 5.22 (d, 1H, H in the 6-position); 5.82 (dd, 1H, H in the 7-position); 6.74 (s, 1H, H of the thiazole nucleus); 7.10 (d, J = 16, 1H, —CH=CHS—); 7.18 (s, 2H, NH₂); 7.26 (d, J = 16, 1H, —CH=CHS—); 7.83 (mt, 3H, p- and m-protons of —C₆H₅); 8.0 (d, J = 7, 2H, o-protons of —C₆H₅); 9.61 (d, J = 9, 1H, —CONH—) |

| | | | | |
|---|---|---|---|---|
| AR | 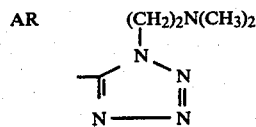 | —CH$_3$ | syn isomer, E form | Product obtained as the formate<br>(1) 3,400, 3,200, 2,000, 1,770, 1,670, 1,615, 1,530, 1,035<br>(2) 2.70 (s, 6H, —N(CH$_3$)$_2$); 2.75 (t, J = 7, 2H, —CH$_2$N$\langle$ ); 3.85 (s, 3H, =NOCH$_3$); 3.95 (t, J = 7, 2H, —CH$_2$CH$_2$N(CH$_3$)$_2$); 5.16 (d, J = 4, 1H, H in the 6-position); 5.85 (dd, J = 4 and 9, 1H, H in the 7-position) 6.74 (s, 1H, H of the thiazole); 6.80 (d, J = 16, 1H, —CH=CHS—); 6.90 (d, J = 16, 1H, =CHS—); 7.20 (s, 2H, —NH$_2$); 9.63 (d, J = 9, 1H, —CONH—) |
| AS | 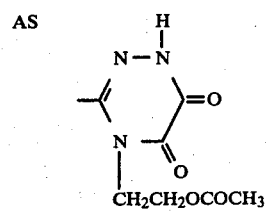 | —CH$_3$ | syn isomer, E form | (1) 3,320, 3,220, 3,150, 2,300, 1,780, 1,740, 1,720, 1,680, 1,635, 1,590, 1,535, 1,375, 1,210, 1,040, 950<br>(2) 2.0 (s, 1H, CH$_3$CO$_2$—); 3.63 and 3.82 (AB-type, J = 18, 2H, —SCH$_2$—); 3.85 (s, 3H, =NOCH$_3$); 4.08 (t, J = 5, 2H, $\rangle$NCH$_2$CH$_2$OCOCH$_3$); 4.25 (t, J = 5, 2H, $\rangle$NCH$_2$CH$_2$OCOCH$_3$); 5.20 (d, J = 4, 1H, H in the 6-position); 5.78 (dd, J = 4 and 9, 1H, H in the 7-position); 6.73 (s, 1H, H of the thiazole); 6.90 (d, J = 16, 1H, —CH=CH—S—); 7.12 (d, J = 16, 1H, —CH=CHS—); 7.18 (s broad, 2H, —NH$_2$); 9.60 (s, J = 9, 1H, —CONH—C$_7$); 12.6 (s broad, 1H, —N=C—OH triazine). |
| AT | 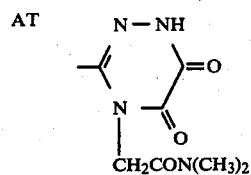 | —CH$_3$ | syn isomer, E form | (1) 3,420, 3,320, 3,210, 1,780, 1,720, 1,690 1,660, 1,530, 1,040, 945<br>(2) 2.88 and 3.08 (2s, 2 × 3H, —CON(CH$_3$)$_2$); 3.61 and 3.82 (2d, J = 18, 2H, —SCH$_2$—); 3.85 (s, 3H, =NOCH$_3$); 4.80 (s broad, 2H, —CH$_2$CON$\langle$ ); 5.21 (d, J = 4, 1H, H in the 6-position); 5.79 (dd, J = 4 and 9, 1H, H in the 7-position); 6.75 (s, 1H, H thiazole); 6.88 and 7.10 (2d, J = 16, 2H, —CH=CH—S—); 7.19 (s broad, 2H, —NH$_2$); 9.60 (d, J = 9, 1H, —CONH—C$_7$—); 12.73 (s, 1H, —N=C—OH or —NH—C— triazine) |
| AU | 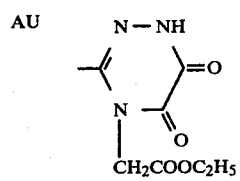 | —CH$_3$ | syn isomer, E form | (1) 3,340, 3,220, 3,130, 1,780, 1,725, 1,690, 1,590, 1,530, 1,040, 945<br>(2) 1.22 (t, J = 7, 3H, CH$_3$—CH$_2$—); 3.60 and 3.85 (2d, J = 18, 2H, —SCH$_2$—); 3.85 (s, 3H, —OCH$_3$); 4.15 (q, J = 7, 2H, —OCH$_2$—CH$_3$); 4.66 (s, 2H, $\rangle$N—CH$_2$CO—); 5.18 (d, J = 4, 1H, H in the 6-position); 5.77 (dd, J = 4 and 11, 1H, H in the 7-position); 6.72 (s, 1H, H of the thiazole); 6.87 (d, J = 16, 1H, —CH=CHS); 7.08 (d, J = 16, 1H, —CH=CHS—); 7.15 (s broad, 2H, —NH$_2$); 9.58 (d, J = 9, 1H, —CONH—); 12.80 (s, 1H, =NNHCO— or =N—N=C—) <br>                                          OH |

| | | | | |
|---|---|---|---|---|
| AV | 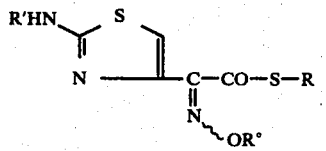 | —CH₃ | syn isomer, E form | (1) 3,405, 3,260, 1,770, 1,710, 1,680, 1,585, 1,530, 1,040, 940, 700 |

We claim:

1. A thioloester of the formula:

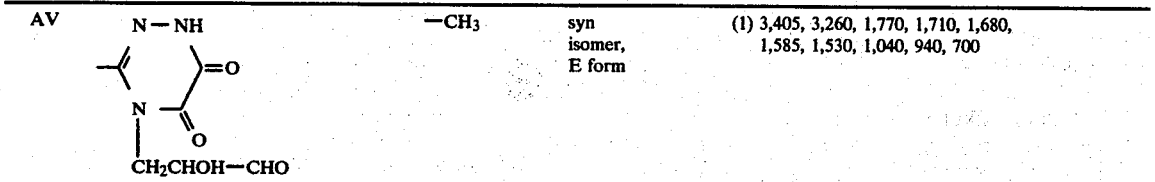

wherein R represents:

(1) alkyl, L-2-amino-2-carboxyethyl or phenyl;

(2) pyrid-2-yl, pyrid-3-yl or pyrid-4-yl or their N-oxides;

(3) pyrimidin-2-yl, pyridazin-3-yl substituted in the 6-position by an alkyl, methoxy, amino or alkanoylamino radical and optionally N-oxidised, or tetrazolo[4,5-b]pyridazin-6-yl;

(4) 5,6-dioxo-1,4,5,6-tetrahydro-1,2,4-triazin-3-yl substituted in the 4-position, or 1,3,4-triazol-5-yl or 2-alkoxycarbonyl-1,3,4-triazol-5-yl substituted in the 1-position, (a) by an alkyl radical which is unsubstituted or substituted by an alkoxy, alkylthio, phenyl, carbamoyl, alkylcarbamoyl, dialkylcarbamoyl, alkanoyl, alkoxycarbonyl or thiazolidin-2-yl radical, (b) by an allyl, 2,3-dihydroxypropyl, 1,3-dihydroxyprop-2-yl, 3-formyloxy-2-hydroxypropyl, 2,3-bis-formyloxypropyl or 1,3-bis-formyloxyprop-2-yl radical, (c) by an alkyl radical containing 2 to 4 carbon atoms and substituted by a hydroxy or carbamoyloxy radical, an alkanoyloxy radical (in which the alkanoyl moiety can be substituted by an amino, alkylamino or dialkylamino radical), an alkylsulphinyl, alkylsulphonyl, amino, alkylamino, dialkylamino, sulphoamino, alkylsulphonylamino or sulphamoylamino radical, an alkanoylamino radical (in which the alkanoyl moiety is optionally substituted by hydroxy, amino, alkylamino or dialkylamino) or an alkoxycarbonylamino, ureido, alkylureido or dialkylureido radical, (d) by a radical of the formula:

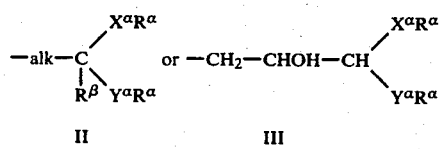

wherein alk represents an alkylene radical containing 1 to 4 carbon atoms, $X^\alpha$ and $Y^\alpha$ are identical and represent oxygen or sulphur atoms and $R^\alpha$ represents an alkyl radical, or alternatively $X^\alpha$ and $Y^\alpha$ are identical or different and represent oxygen or sulphur atoms and the radicals $R^\alpha$ together form an alkylene radical containing 2 or 3 carbon atoms;

and $R^\beta$ represents a hydrogen atom or an alkyl radical containing 1 to 3 carbon atoms, or (e) by an alkyl radical containing 2 to 5 carbon atoms and substituted by an alkoxyimino or hydroxyimino radical;

(5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl;

(6) 1,3,4-triazol-5-yl, 1,2,3-triazol-5-yl or 1-alkyl-1,2,4-triazol-5-yl which is unsubstituted or substituted in the 3-position by alkoxycarbonyl;

(7) (a) 1,3,4-thiadiazol-5-yl which is unsubstituted or substituted by an alkyl, trifluoromethyl, alkoxy or alkylthio radical, a hydroxyalkylthio radical in which the alkyl moiety contains 2 to 4 carbon atoms, or an alkylsulphonyl, hydroxy, hydroxyalkyl, carboxy, carboxyalkyl, amino, alkylamino, dialkylamino, aminoalkyl, alkylaminoalkyl, dialkylaminoalkyl, alkanoylamino or alkanoylaminoalkyl radical, or (b) 1,2,4-thiadiazol-5-yl substituted by an alkyl or alkoxy radical;

(8) (a) 1,3,4-oxadiazol-5-yl which is unsubstituted or substituted by an alkyl, trifluoromethyl, phenyl, aminoalkyl, alkylaminoalkyl, dialkylaminoalkyl or alkanoylaminoalkyl radical, or (b) oxazol-2-yl or 4-alkyloxazol-2-yl; or (9) tetrazol-5-yl which is unsubstituted or substituted in the 1-position by (a) an alkyl radical which is unsubstituted or substituted by alkoxy, sulpho, carboxy or sulphamoyl, (b) an alkyl radical containing 2 to 4 carbon atoms and substituted by hydroxy, amino, alkylamino, dialkylamino, alkanoylamino, carboxyalkylamino, sulphamoylamino, sulphoamino, ureido, alkylureido or dialkylureido, (c) an alkyl radical containing 2 to 5 carbon atoms and substituted by hydroxyimino or alkoxyimino, (d) a phenyl, 2,3-dihydroxypropyl, 1,3-dihydroxyprop-2-yl, 3-formyloxy-2-hydroxypropyl, 2,3-bis-formyloxypropyl or 1,3-bis-formyloxyprop-2-yl radical, or (e) a radical of formula II wherein $R^\beta$ represents a hydrogen atom, or a radical of formula III; R° represents a hydrogen atom, an alkyl, vinyl or cyanomethyl radical, or an oxime-protecting radical selected from trityl, tetrahydropropyranyl or 2-methoxyprop-2-yl and R' represents a hydrogen atom or an amine-protecting radical selected from t-butoxycarbonyl, 2,2,2-trichloroethoxycarbonyl, trichloroacetyl, trityl, benzyl, dibenzyl, benzyloxycarbonyl, p-nitrobenzyloxycarbonyl, p-methoxybenzyloxycarbonyl, chloroacetyl, trifluoroacetyl and formyl; it being understood that when R represents L-2-amino-2-carboxyethyl, 6-aminopyridazin-3-yl, or R represents 5,6-dioxo-1,4,5,6 tetrahydro-1,2,4 triazin-3-yl substituted in the 4-position, or 1,3,4-triazol-5-yl or 2-alkoxycarbonyl-1,3,4-triazol-5-yl substituted in the 1-position by an alkyl radical containing 2 to 4 carbon atoms which is substituted by amino, alkylamino, aminoalkanoyloxy, alkylaminoalkanoyloxy, aminoalkanoylamino, alkylaminoalkanoylamino, or R represents 1,3,4-thiadiazol-5-yl substituted by amino, alkylamino, aminoalkyl or alkylaminoalkyl, or R represents 1,3,4-oxadiazol-5-yl substituted by aminoalkyl or alkylaminoalkyl, or R represents tetrazol-5-yl substituted in the 1-position by an alkyl radical containing 2 to 4 carbon atoms which is substituted by amino, alkylamino, carboxyalkylamino, the amino or alkylamino group is protected by an amine protecting radical selected from the groups hereinbefore defined for R';

when R represents L-2-amino-2-carboxyethyl, 1,3,4-thiadiazol-5-yl substituted by carboxy or carboxyalkyl or R represents tetrazol-5-yl substituted in the 1-position by a carboxyalkyl or by an alkyl radical containing 2 to 4 carbon atoms and substituted by carboxyalkylamino, said carboxy can be protected by an acid-protecting radical selected from methoxymethyl, t-butyl, benzhydryl, p-nitrobenzyl or p-methoxybenzyl;

when R represents 5,6-dioxo-1,4,5,6-tetrahydro-1,2,4-triazin-3-yl substituted in the 4-position or 1,3,4-triazol-5-yl or 2-alkoxycarbonyl-1,3,4-triazol-5-yl substituted in the 1-position by 3-formyloxy-2-hydroxypropyl or by an alkyl radical containing 2 to 4 carbon atoms substituted by hydroxy or hydroxyalkanoylamino or by a radical of the formula III, or by a hydroxyiminoalkyl radical containing 2 to 5 carbon atoms, or R represents 1,3,4-thiadiazol-5-yl substituted by hydroxy or hydroxyalkyl, or by hydroxyalkylthio containing 2 to 4 carbon atoms, or R represents tetrazol-5-yl substituted in the 1-position by hydroxyalkyl containing 2 to 4 carbon atoms or by hydroxyiminoalkyl containing 2 to 5 carbon atoms or by 3-formyloxy-2-hydroxypropyl or by a radical of formula III, the hydroxy group can be protected by a hydroxy-protecting radical selected from trityl, tetrahydropyranyl and 2-methoxyprop-2-yl, and when R represents 5,6-dioxo-1,4,5,6-tetrahydro-1,2,4 triazin-3-yl substituted in the 4-position or 1,3,4-triazol-5-yl or 2-alkoxycarbonyl-1,3,4-triazol-5-yl or tetrazol-5-yl substituted in the 1-position by 2,3-dihydroxypropyl or by 1,3-dihydroxyprop-2-yl, the hydroxy groups can be protected both in the form of a 2,2-dimethyldioxolan-4-yl methyl or 2,2-dimethyldioxan-5-yl radical, and that the alkyl and alkanoyl moieties or radicals mentioned above are linear or branched and unless otherwise specified contain from 1 to 4 carbon atoms; its syn or anti isomer or a mixture thereof, and, when R contains a carboxy or sulpho radical, a metal salt thereof or an addition salt thereof with a tertiary nitrogen-containing base.

2. A thioloester according to claim 1, wherein R represents:

(1) optionally N-oxidised pyrid-2-yl;

(2) pyrimidin-2-yl or pyridazin-3-yl substituted in the 6-position by a methyl radical and optionally N-oxidised;

(3) 5,6-dioxo-1,4,5,6-tetrahydro-1,2,4-triazin-3-yl substituted in the 4-position by (a) an alkyl radical containing 1 to 3 carbon atoms or an alkyl radical containing 1 or 2 carbon atoms and substituted by an alkoxy, alkylthio, phenyl, carbamoyl, dialkylcarbamoyl or alkoxycarbonyl radical, (b) an allyl or 2,3-dihydroxypropyl radical, (c) an alkyl radical containing 2 or 3 carbon atoms and substituted by hydroxy, carbamoyloxy, alkanoyloxy (unsubstituted or substituted by amino), amino or alkanoylamino (unsubstituted or substituted by amino), or (d) a radical of the formula II or III in which alk represents alkylene containing 1 or 2 carbon atoms, $X^\alpha$ and $Y^\alpha$ represent oxygen atoms, $R^\alpha$ represents an alkyl radical and $R^\beta$ represents a hydrogen atom;

(4) 2-alkoxycarbonyl-1,3,4-triazol-5-yl substituted in the 1-position by a radical of formula II as defined in 3(d) above;

(5) 1,4-dialkyl-5,6-dioxo-1,4,5,6-tetrahydro-1,2,4-triazin-3-yl, 1-alkyl-5,6-dioxo-1,4,5,6-tetrahydro-1,2,4-triazin-3-yl or 2-alkyl-5,6-dioxo-1,2,5,6-tetrahydro-1,2,4-triazin-3-yl;

(6) 1-alkyl-3-alkoxycarbonyl-1,2,4-triazol-5-yl;

(7) (a) 1,3,4-thiadiazol-5-yl which is unsubstituted or substituted by an alkyl, amino, dialkylaminoalkyl or alkanoylaminoalkyl radical, or (b) 1,2,4-thiadiazol-5-yl substituted by an alkyl radical;

(8) (a) 1,3,4-oxadiazol-5-yl substituted by a phenyl radical, or (b) 4-alkyloxazol-2-yl; or (9) tetrazol-5-yl substituted in the 1-position by (a) an alkyl radical, (b) an alkyl radical containing 2 or 3 carbon atoms and substituted by hydroxy, dialkylamino or, alkanoylamino, or (c) a radical of formula II as defined in 3(d) above;

the symbol R° represents a hydrogen atom or a methyl, vinyl or cyanomethyl radical and the symbol R' represents a trityl radical, it being understood that the abovementioned alkyl or alkanoyl moieties or radicals unless otherwise specified contain 1 or 2 carbon atoms, and that the amino or alkylamino groups are protected by a t-butoxycarbonyl radical and the hydroxy groups are protected by a trityl or 2-methoxyprop-2-yl radical, or by a 2,2-dimethyldioxolan-4-yl-methyl radical in the case of the protection of a 2,3-dihydroxypropyl radical; and its syn or anti isomer or a mixture thereof.

3. A thioloester according to claim 1 wherein R represents:

(1) 5,6-dioxo-1,4,5,6-tetrahydro-1,2,4-triazin-3-yl substituted in the 4-position by (a) alkyl containing 2 to 4 carbon atoms and substituted by t-butoxycarbonylamino or alkanoylamino, or (b) a radical of formula II as defined in claim 1;

(2) 2-alkyl-1,3,4-thiadiazol-5-yl; or (3) 1-alkyltetrazol-5-yl;

R° is a methyl radical and R' is a trityl radical, it being understood that the abovementioned alkyl and alkanoyl radicals and moieties unless otherwise specified contain 1 or 2 carbon atoms; its syn or anti isomer or a mixture thereof.

4. A thioloester according to claim 1 wherein the group —OR° in general formula I depicted in claim 1 is in the syn-configuration.

5. A compound according to claim 1 which is the syn isomer of 5-[2-methoxyimino-2-(2-tritylaminothiazol-4-yl)-acetylthio]-2-methyl-1,3,4-thiadiazole.

6. A compound according to claim 1 which is the syn isomer of 4-(2,2-dimethoxyethyl)-5,6-dioxo-3-[2-methoxyimino-2-(2-tritylaminothiazol-4-yl)-acetylthio]-1,4,5,6-tetrahydro-1,2,4-triazine.

7. A compound according to claim 1 which is the syn isomer of 4-(2-t-butoxycarbonyl-aminoethyl)-5,6-dioxo-3-[2-methoxyimino-2-(2-tritylaminothiazol-4-yl)-acetylthio]-1,4,5,6-tetrahydro-1,2,4-triazine.

8. A compound according to claim 1 which is the syn isomer of 5-[2-methoxyimino-2-(2-tritylaminothiazol-4-yl)-acetylthio]-1-methyltetrazole.

9. A compound according to claim 1 which is the syn isomer of 4-(2-acetamidoethyl)-5,6-dioxo-3-[2-methoxyimino-2-(2-tritylaminothiazol-4-yl)-acetylthio]-1,4,5,6-tetrahydro-1,2,4-triazine.

10. A thiolester of the formula:

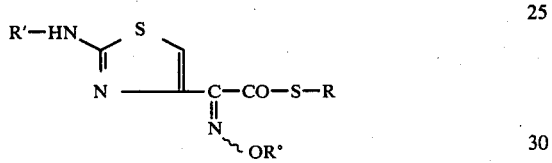

wherein R is selected from the group consisting of 1,4-dialkyl-5, 6-dioxo-1,4,5,6-tetrahydro-1,2,4-triazin-3-yl, 1-alkyl-5,6-dioxo-1,4,5,6-tetrahydro-1,2,4-triazin-3-yl,2-alkyl-5,6-dioxo-1,2,5,6-tetrahydro-1,2,4-triazin-3-yl, and 5,6-dioxo-1,4,5,6-tetrahydro-1,2,4-triazin-3-yl substituted in the 4-position with (a) an unsubstituted alkyl radical or a substituted alkyl radical substituted with an alkoxy, alkylthio, phenyl, carbamoyl, alkylcarbamoyl, dialkylcarbamoyl, lower alkanoyl, alkoxycarbonyl or thiazolidin-2-yl radical;

(b) allyl, 2,3-dihydroxypropyl, 1,3-dihydroxy prop-2-yl, 3-formyloxy-2-hydroxypropyl, 2,3-bis-formyloxypropyl or 1,3-bis-formyloxyprop-2-yl;

(c) $C_2$–$C_4$ alkyl substituted with hydroxy or carbamoyloxy, lower alkanoyloxy, lower alkanoyloxy wherein the lower alkanoyl moiety is substituted with an amino, alkylamino or dialkylamino, alkylsulphinyl, alkysulphonyl, amino, alkylamino, dialkylamino, sulphoamino, alkylsulphonylamino, sulphamoylamino, lower alkanoylamino, substituted lower alkanoylamino wherein the lower alkanoyl moiety is substituted with hydroxy, amino, alkylamino, or dialkylamino, alkoxycarbonylamino, ureido, alkylureido, or dialkylureido;

(d) a radical of the formula

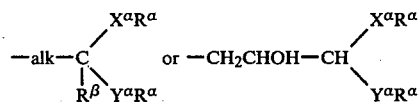

wherein alk is $C_1$–$C_4$ alkylene, $X^\alpha$ and $Y^\alpha$ are identical and represent oxygen or sulphur atoms and $R^\alpha$ represents alkyl or alternatively $X^\alpha$ and $Y^\alpha$ are identical or different and represent oxygen or sulphur atoms and the radicals $R^\alpha$ together form an alkylene radical containing 2 or 3 carbon atoms, and $R^\beta$ represents a hydrogen atom or $C_1$–$C_3$ alkyl, or (e) $C_2$–$C_5$ alkyl substituted with an alkoxyimino or hydroxyimino radical;

R° is a hydrogen atom, alkyl, vinyl, cyanomethyl or an oxime-protecting radical as defined in claim 1 and R' is an amine-protecting radical as defined in claim 1;

it being understood that when R represents 5,6-dioxo-1,4,5,6-tetrahydro-1,2,4-triazin-3yl substituted in the 4-position with $C_2$–$C_4$ alkyl itself substituted by amino, alkylamino, lower alkanoyloxy wherein the alkanoyl moiety is substituted with amino or with alkylamino or lower alkanoylamino wherein the alkanoyl moiety is substituted with amino or with alkylamino, the amino or alkyl amino group is protected by an amine-protecting radical as defined in claim 1; when R represents 5,6-dioxo-1,4,5,6-tetrahydro-1,2,4-triazin-3-yl substituted in the 4-position with 3-formyloxy-2-hydroxypropyl or $C_2$–$C_4$ alkyl itself substituted with hydroxy or with hydroxysubstituted lower alkanoylamino, or a radical of the formula

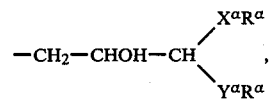

or $C_2$–$C_5$ alkyl itself substituted with hydroxyimino, the hydroxy group can be protected by a hydroxy-protecting radical as defined in claim 17; and when R represents 5,6-dioxo-1,4,5,6-tetrahydro-1,2,4 triazin-3-yl substituted in the 4-position with 2,3-dihydroxypropyl or 1,3-dihydroxyprop-2-yl, the hydroxy groups can be protected both in the form of a 2,2-dimethyldioxolan-4-ylmethyl or 2,2-dimethyldioxan-5-yl radical, and that the alkyl and lower alkanoyl moieties or radicals mentioned above are linear or branched and unless otherwise specified contain 1 to 4 carbon atoms; its syn or anti isomer or a mixture thereof, and when R contains a sulpho radical, a metal salt thereof or an addition salt thereof with a tertiary nitrogen-containing base.

* * * * *